United States Patent
Goodman et al.

(10) Patent No.: US 6,627,154 B1
(45) Date of Patent: Sep. 30, 2003

(54) ELECTRONIC TECHNIQUES FOR ANALYTE DETECTION

(75) Inventors: Rodney M. Goodman, Altadena, CA (US); Vincent Koosh, Pasadena, CA (US); Jeffrey Dickson, Pasadena, CA (US)

(73) Assignee: Cyrano Sciences Inc., Pasadena, CA (US)

(*) Notice: Subject to any disclaimer, the term of this patent is extended or adjusted under 35 U.S.C. 154(b) by 0 days.

(21) Appl. No.: 09/287,522

(22) Filed: Apr. 7, 1999

Related U.S. Application Data

(63) Continuation of application No. 09/276,988, filed on Mar. 26, 1999, now Pat. No. 6,495,892.
(60) Provisional application No. 60/092,707, filed on Jul. 14, 1998, and provisional application No. 60/081,182, filed on Apr. 9, 1998.

(30) Foreign Application Priority Data

Aug. 7, 1998 (WO) .................................. PCT/US/16527

(51) Int. Cl.[7] .............................................. G01N 27/00
(52) U.S. Cl. ................ 422/82.01; 422/68.1; 422/82.02; 422/83; 436/149; 436/150; 436/151
(58) Field of Search ........................... 436/151; 357/30; 250/578.1, 578; 257/369; 422/68.1, 82.01, 82.02, 83; 204/422, 424, 452; 205/787

(56) References Cited

U.S. PATENT DOCUMENTS

| | | | |
|---|---|---|---|
| 3,964,083 A | * | 6/1976 | Lohstroh ...................... 357/30 |
| 4,388,532 A | * | 6/1983 | Garcia ........................ 250/578 |
| 4,728,882 A | | 3/1988 | Stanbro et al. ........... 324/61 R |
| 4,822,566 A | | 4/1989 | Newman ...................... 422/68 |
| 4,874,500 A | | 10/1989 | Madou et al. ............... 204/412 |
| 4,935,207 A | | 6/1990 | Stanbro et al. ............ 422/68.1 |
| 4,935,636 A | * | 6/1990 | Gural ...................... 250/578.1 |
| 5,305,231 A | | 4/1994 | Coppler et al. |
| 5,345,213 A | | 9/1994 | Semancik et al. |
| 5,527,711 A | | 6/1996 | Tom-Moy et al. .......... 436/518 |
| 5,571,401 A | | 11/1996 | Lewis et al. ................ 205/787 |
| 5,872,380 A | * | 2/1999 | Rostocker et al. .......... 257/369 |

FOREIGN PATENT DOCUMENTS

| | | |
|---|---|---|
| EP | 0774662 A1 | 5/1997 |
| WO | WO 93/22678 A2 | 11/1993 |

OTHER PUBLICATIONS

Diorio et al., "A floating–gate MOS learning array with locally computed weight updates" IEEE Transactions on Electronic Devices (1997) 44(12):2281–2289.

Persaud et al., "Design strategies for gas and odour sensors which mimic the olfactory systems" NATO ASI Series F: Computer and System Sciences (1993) 102:579–602.

* cited by examiner

*Primary Examiner*—Jill Warden
*Assistant Examiner*—Brian Sines
(74) *Attorney, Agent, or Firm*—Townsend and Townsend and Crew LLP

(57) ABSTRACT

Techniques are used to detect and identify analytes. Techniques are used to fabricate and manufacture sensors to detect analytes. An analyte (1810) is sensed by sensors (1820) that output electrical signals in response to the analyte. The electrical signals are preprocessed (1830) by filtering and amplification. In an embodiment, this preprocessing includes adapting the sensor and electronics to the environment in which the analyte exists. The electrical signals are further processed (1840) to classify and identify the analyte, which may be by a neural network.

8 Claims, 16 Drawing Sheets

ELECTRONIC TECHNIQUES FOR ANALYTE DETECTION

CROSS-REFERENCES TO RELATED APPLICATIONS

This application claims the benefit of U.S. provisional application Nos. 60/081,182, filed Apr. 9, 1998, and 60/092,707, filed Jul. 14, 1998, and is a continuation of U.S. patent application Ser. No. 09/276,988, filed Mar. 26, 1999 now U.S. Pat. No. 6,495,892.

STATEMENT AS TO RIGHTS TO INVENTIONS MADE UNDER FEDERALLY SPONSORED RESEARCH AND DEVELOPMENT

The research carried out in this application was supported in part by grants from the United States Army (#DAAG55-97-1-0187), DARPA (#DAAK60-97-K-9503), and the National Science Foundation (CHE 9202583). The U.S. government may have rights in any patent issuing from this application.

BACKGROUND OF THE INVENTION

The field of the invention relates to techniques for the detection and identification of an analytes, and in a specific embodiment, electronic olfaction.

Human beings have five classical senses—sight, smell, taste, hearing, and touch. Since the earliest times, humankind has sought techniques and devices for enhancing and extending these senses. Many of the devices and instruments that have been developed to extend human perception are considered among of the most revolutionary inventions in history. These inventions have had a profound impact on human civilization and have led to many additional breakthroughs and discoveries. Just a few of the many instruments developed to extend the reach of human perception include the telescope, microscope, stethoscope, X-rays, radio, audio amplifier, scanning electron microscope, night-vision goggles, and many others.

As can be expected, there has been considerable interest in developing a device or instrument for the general detection of analytes in a fluid, vacuum, air, or other medium. A specific instance of an analyte detector is a device for sensing smell or odors (i.e., analytes in air). It is well recognized that some animals like dogs have a keener sense of smell than human beings. Because of their "noses," dogs have been utilized for many tasks including, for example, the detection of bombs, mines, drugs, poison gases, and illegal contraband; dogs also aid in the search and rescue of humans. Devices for sensing smell would be useful for the traditional applications where animals are used, as well as for a multitude of uses where animals are impractical or inappropriate.

Moreover, a device for the general detection of analytes has potentially many more applications than a specific device for detecting smells. For example, the uses for a device for analyte detection include the detection of chemical leaks, quality control in food processing, medical diagnosis and testing, fabrication and manufacture of commercial and industrial goods, pharmaceutical production, testing or evaluating any odorant or analyte in any medium (e.g., fuel, oil, wine, solvents), and many other applications. An instrument for analyte detection would be highly desirable in industries and applications such as the chemical and petrochemical sectors, food, fragrance, medical, automotive, military, environmental, health and safety, and indoor air quality.

Therefore, it is desirable to develop techniques and devices for the detection of analytes. An approach for sensing smells is to use surface acoustic wave (SAW) resonators. However, the signal transduction mechanism for SAW devices has many shortcoming because these devices utilize relatively complicated electronics, which are somewhat costly. Furthermore, SAW devices are generally extremely sensitive to both mass and acoustic impedance changes, and may not be suitable for use in all environments.

Therefore, there is a need for techniques and systems for analyte detection, especially ones that are relatively low cost, easy to manufacture, provide rapid response, and produce accurate differentiation between different analytes and different concentrations of the same analyte.

SUMMARY OF THE INVENTION

The present invention provides techniques and a system for detecting and identifying analytes in fluids. Techniques for fabricating and manufacturing sensors to detect analytes are also provided. Analytes may include smells, tastes, vapors, odors, gases, fluids, liquids, and chemicals, among others. The analyte may be in air, fluid, or other medium. In the present invention, an analyte is sensed by sensors that output electrical signals in response to the analyte. The electrical signals may be preprocessed by filtering and amplification. This preprocessing may also include adapting the sensor and electronics to the environment in which the analyte exists. The electrical signals may be further processed to classify and identify the analyte.

In a specific embodiment, the present invention is used to implement an electronic olfaction system or "synthetic nose." This system will perform an analogous function as a mammalian olfactory system, although the electronic system will have additional capabilities. Such an electronic nose system will reveal the identification and concentration of vapors. Another embodiment for the analyte detection system of the present invention is used to implement a device for tasting. This device would function similarly to a mammalian tongue. There are many other possible specific applications of the techniques of the present invention, too numerous to name here.

Sensors of the present invention are fabricated on a substrate or other suitable material. For example, in one embodiment, the sensors are formed using semiconductor processing techniques on a single integrated circuit. The integrated circuit or chip contains a plurality of sensors, each contained at a sensor site. The sensor sites may be arranged in rows and columns. Structures or other means are constructed on the substrate to constrain a sensor material at each sensor site. For example, the sensor sites may be a plurality of sensor wells that will hold the sensor material.

The sensor material applied to or formed at one sensor site may have a different composition from the sensor material at a different site. For example, each sensor in the analyte detection system may have a different composition from every other sensor. The sensor material may be a mixture of a nonconductive material and a conductive material such as carbon black; the composition or concentration of carbon black will vary for each sensor on the chip. By providing a system of diverse sensors, each sensor may have a different response characteristic for a given analyte. The sensor's response to an analyte can be characterized by a measurable change in an electrical property such as resistance, capacitance, or inductance.

There is also an electrical connection at each sensor site to route the electrical signals from the sensor material to other circuitry for further processing. The circuitry may be on-chip with the sensors, or may be off-chip, such as on a different integrated circuit. The data from the sensors may be processed using a computer. In a specific embodiment, the circuitry for each sensor site is formed beneath or interspersed with the sensor sites on the integrated circuit.

The electrical signals from the sensors are further processed to classify the response to the analyte. The processing electronics may include electronic circuits to amplify and enhance the received data from the sensors. Each analyte may have a particular "fingerprint." The analyte will be identified based on this fingerprint. The signal processing for the identification and classification of the analyte is performed by on-chip or off-chip electronic circuitry. For example, classification is performed using a neural network, among other techniques. Therefore, using the techniques and system of the present invention, an analyte can be distinguished and identified.

An aspect of the present invention is the use of a number of sensors to detect analytes. A further aspect of the present invention is the use of an integrated circuit having an array of sensors to detect analytes. A still further aspect of the present invention is the use of a semiconductor process to fabricate an integrated circuit having an array of sensors used to identify an analyte. The present invention includes the use of electronic circuitry to process the electrical signals from a plurality of analyte sensors to identify an analyte, where each sensor includes a mixture of nonconductive organic material and a conductive material.

In a specific embodiment, the present invention is an integrated circuit including a plurality of sensor sites formed on a substrate, each sensor site for constraining the sensor material. The integrated circuit further includes an electrical terminal formed to measure an electrical property of the sensor material. The electrical property is an impedance, resistance, capacitance, inductance, or other electrical property. The sensor material may be a mixture of a nonconductive organic material and a conductive material.

In a further embodiment, the present invention includes receiving data from a number of sensors for detecting chemical analytes, where each sensor has a first and second output terminal. There are plurality of electronic circuits, coupled to receive the electrical data from the first and second output terminals of the sensor. This electrical data may be an analog weight. The electrical circuitry may include a floating gate device such as a Flash or EEPROM cell to store the analog weight. The electrical data (e.g., analog weights) is further used to identify the analyte. The identification scheme may include use of a neural network.

Other objects, features, and advantages of the present invention will become apparent upon consideration of the following detailed description and the accompanying drawings, in which like reference designations represent like features throughout the figures.

DETAILED DESCRIPTION

Figure 1:
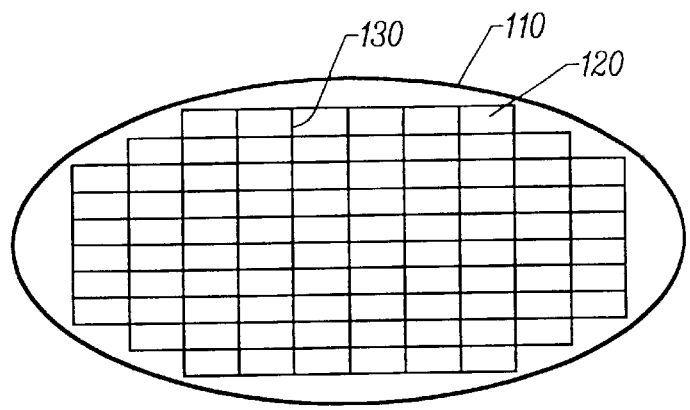
FIG. 1 shows a substrate with a number of analyte detection integrated circuits.

The present invention provides techniques for the detection and identification of analytes. These analytes may be in fluids, which may be liquid or gaseous in nature. The techniques of the present invention may also be used to provide other information about analytes, including for example, the concentration, classification, volume, flow rate, direction of a plume trail, location of source of analyte, gradient, and other characteristics. For example, the techniques of the present invention may allow the determination of the concentration of a first analyte and a second analyte in a mixture.

A system of analyte detection of the present invention has many applications. This system may be embodied within analytical instruments, handheld devices, robots, and many other devices and tools. For example, the system of the present invention may, in a specific implementation, reside on a single integrated circuit or multiple integrated circuits. There are however many other ways to implement a system of the present invention. For example, the system of the present invention may have components which are relatively close in proximity to another, such as being resident on the same substrate, integrated circuit, or printed circuit (PC) board. Alternatively, various components of the analyte detection system may also reside in different locations, and linked by a network or other communications link. This network may include a local-area network, wide-area network, wireless network, cellular phone network, optical network, the internet, electrical wire, and many others, and combinations of these networks.

An example of a specific embodiment of the present invention is an electronic system of analyte detection. In particular, the electronic system of analyte detection may include a plurality of sensors. Further, one sensor in the plurality of sensors may have a different characteristic from another sensor in the plurality. In an even further embodiment, each sensor in the plurality of sensors may have different characteristics from every other sensor. U.S. Pat. No. 5,571,401 discusses sensors and sensor materials which may be used in a system of the present invention, although other sensors and sensor materials may also be used. U.S. Pat. No. 5,571,401 is incorporated by reference in its entirety for all purposes.

A technology that has led to the proliferation of modern electronics is the integrated circuit. Integrated circuit technology may be used in an electronic analyte detection system of the present invention. However, the present invention is not necessarily limited to integrated circuit technology, as there are many other technologies for implementing the present invention. For example, the system of the present invention may be practiced using discrete electronic components assembled on a printed circuit board. A system of the present invention may be contained within a handheld electronic device.

Using integrated circuit technology to fabricate an electronic analyte detection device permits relatively low cost and high volume manufacture of such devices. Integrated circuits are the modern marvel of today's electronic and information age. Commonly referred to as "chips," integrated circuits are miniaturized electronic circuits fabricated on silicon substrates. Chips are commonplace in the electronics market, and are the building blocks for a vast number of electronic products used in many industries. Products using integrated circuits include computers, computer peripherals, consumer electronics, telecommunications and networking equipment, and many others.

A system of the present invention may be manufactured using integrated circuit technology. However, the present invention is not necessarily limited to implementations using integrated circuit technology; other technologies may also be used. The present invention is also not limited to electronic olfaction since a system according to the present invention may be used to detect, identify, and classify analytes in a variety of mediums and environments.

FIG. 1 shows an implementation of the present invention using integrated circuit technology. A substrate or wafer 110 has a number of analyte detection chips 120. Similar to the case with integrated circuit fabrication, many analyte detection chips 120 may be formed on a single substrate. There may be hundreds or thousands of such chips on one substrate.

The substrate may be silicon, such as single crystal silicon having a <100> or <111> orientation. Other materials may also be used as a substrate including, just to name a few, other semiconductive materials, other materials suitable for the manufacture of integrated circuits, insulators, diamond, silicon (or other semiconductor material) over an insulator (such as sapphire), plastic, fused substrates, and polymers.

Analyte detection chips 120 may be fabricated on the substrate using a semiconductor process typical of the integrated circuit industry. Successive layers of various materials are formed and patterned on the substrate. The layers may include, just to name a few examples, diffusion (n- and p-type), silicon oxide, gate oxide, polysilicon, metal (including multiple layers of metal), contact, and via. These layers may be formed on the substrate by deposition, growth, ion implantation, sputtering, electroplating, and other techniques. Photoresist may be used to pattern the features on the substrate. Features may be etched using dry or wet etching techniques, and combinations of these in the same process.

In one embodiment of the present invention, analyte detection chips are fabricated using a CMOS process technology. Many other technologies may also be used, such as NMOS, BiCMOS, bipolar, and others.

Individual analyte detection chips are formed adjacent to other chips on the substrate. Individual chips are separated from each other by a scribe line 130. In many instances, each analyte detection chip is substantially identical to another. It is however possible to manufacture different types or different designs of analyte detection chips on a wafer. There may also be test die or structures on the wafer to allow testing and evaluation of various process parameters and properties of the analyte detection chips during the fabrication of the wafer. Test structures may also be formed in the scribe lines between the individual dies.

During the manufacture of analyte detection chips, a sensor material is placed on the substrate. For example, this sensor material may be deposited, coated, or otherwise applied on the substrate. In one embodiment, the sensor material is any material which provides an electrical response to an analyte or odorant. For example, an electrical response may be quantified in terms of impedance (Z), resistance (R), inductance (L), capacitance (C), or other electrical property. In an embodiment, the sensor material may be a polymer. The material may be organic, or inorganic in other embodiments. Further, the sensor material may consist of regions of a nonconductive organic material and a conductive material. In other embodiments, the sensor material may be insulating organic films that act as capacitors or composite films that act as inductors. A more detailed description of some sensor materials and their properties is discussed in U.S. Pat. No. 5,571,401. However, the present invention is not limited to the sensor materials in U.S. Pat. No. 5,571,401 since other materials may also be used.

In a specific embodiment of the present invention, the sensor technology may involve a series of conductive polymeric composite vapor sensors. The presence of an analyte may be detected through a change in, for example, the electrical resistance of a chemically sensitive carbon-based resistor. As discussed above, changes in electrical properties other than resistance may also be used; these include the evaluation of capacitive and inductance changes.

Further, the sensor material may be composed of conductor and insulator composites. This material may be placed on the substrate in a film. The organic nonconducting polymer of the composite absorbs the analyte (which may be a vapor). This induces a change in the electrical properties of the sensor material. The sensor material may also undergo physical changes such as swelling. When the analyte is removed, any changes in the electrical properties reverse. For example, the resistance, capacitance, and inductance may return to their original value. Any physical changes would also reverse. The response of these types of sensors are reversible over multiple analyte exposures as well as reproducible over a large number of trials under a variety of ambient atmospheric conditions. Therefore, a device fabricated using these types of sensor materials would have a relatively long service life.

In the case of using a composite such a nonconducting polymer and carbon black, the sensor material will be temperature sensitive. When using temperature-sensitive sensors, the sensor should be kept at a relatively constant temperature to provide relatively consistent results. For example, a temperature such as about 5 degrees C. above the ambient should provide good results. Further, extremely high temperatures, say, above about 100 degrees C., should be avoided since these temperatures would destroy the polymer sensor material or rapidly decrease its service life.

For this reason, it is not expected that nonconducting polymer materials are to be used in the specialized environment of extreme high temperatures, say, from about 300 degrees C. to about 400 degrees C. or even higher. The polymer sensor materials will be usable in the normal temperature ranges from about 0 degrees C. to about 100 degrees C.

Using a conductor and insulator composite for the sensor material permits a very broad, diverse collection of sensor materials. For example, any conducting element including carbon blacks, metallic colloids, or organic conducting polymers, and combinations of these, may be used as the conductive phase of the sensors. Any organic material may be used as the insulating phase of the sensors. Furthermore, an advantage of these types of sensor materials is that they do not have the stability limitations of conducting organic polymeric materials. A conductor and insulator composite also does not suffer the limitations from the types of substituents or restrictions on the ranges of swelling variations that can be obtained from backbone modification of pure organic conducting polymers.

After processing of a substrate or wafer is complete, the wafer is tested to determine the number and location of the "good die." The percentage of good die on one wafer compared to the total number of die on the wafer is referred to as the "yield." Individual analyte detection dies are separated by sawing along the scribe lines. The analyte detection dies are then packaged, and may be further tested to ensure their proper operation. These dies may be packaged in a variety of packaging material including ceramic, epoxy, plastic, glass, and many others. Packaged analyte detection die may very much resemble packaged integrated circuit chips. For some types of applications, nonporous, nonreactive materials like ceramic may be used.

In one embodiment, the sensor material is deposited or applied at the wafer level, before individual dies are separated. In other embodiments, the sensor material is applied after the dies are separated.

Figure 2A:
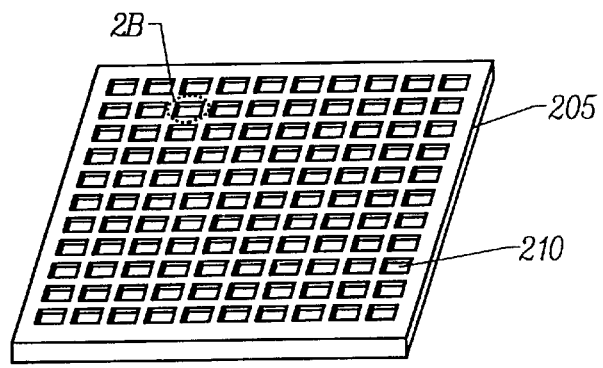
FIG. 2A shows a more detailed diagram of one analyte detection integrated circuit.

FIG. 2A shows a more detailed diagram of an analyte detection chip 205. In a basic embodiment, an analyte detection chip of the present invention includes a plurality of sensor sites 210 of sensor material. In the present invention, the sensor material is constrained by some means at each sensor site. There are many techniques of constraining the sensor material at specific sites on the substrate. For example, the sensor material may be constrained at specific sites by surface tension. The sensor material may also be constrained by an electrical charge, electric field, or magnetic field. Further, the sensor material may be constrained using structures formed by integrated circuit processing techniques or other techniques (e.g., micromachining or microelectromechanical systems (MEMS)). Examples of these structures include sensor wells, ridges, trenches, circular structures, towers, and many structures to constrain the sensor material at the sensor sites. These structures will be fabricated on or in the substrate.

Figure 2B:
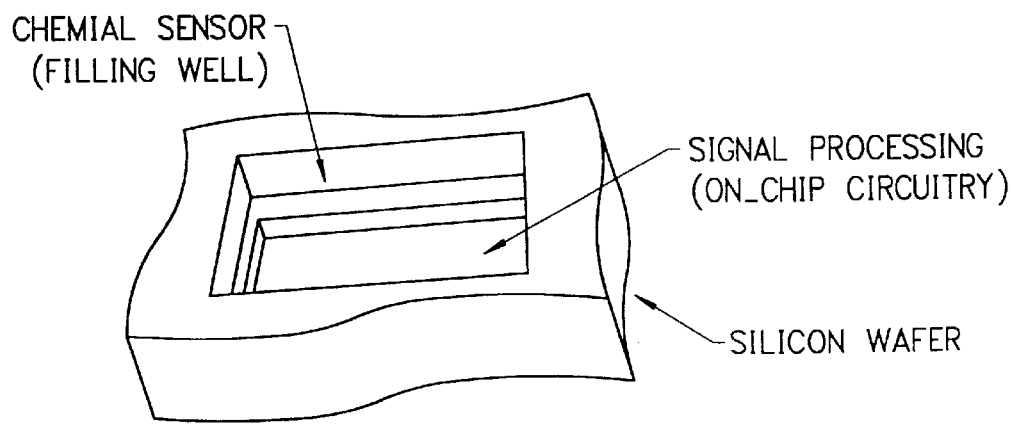
FIG. 2B shows a detailed view of a sensor well.

In the specific embodiment shown in FIGS. 2A and 2B, sensor wells are used to constrain the sensor materials at the sensor sites. FIG. 2B shows a more detailed view of a single sensor well. In the typical case, the sensor material will be deposited in the sensor wells of the analyte detection chips at the wafer level, before the chips are separated from the wafer. The sensor wells, however, may also be filled after the individual chips have been separated from the wafer. As discussed above, other techniques may be used to form the sensor sites and constrain the sensor material, and sensor wells are shown merely as an example. Other structures may be used in a similar fashion to constrain the sensor material.

For the analyte detection chip in FIG. 2A, the sensor sites are arranged in an array having rows and columns of eleven sensor sites by eleven sensor sites, for a total of 121 sensor sites. As discussed above, the sensor sites in FIG. 2A are sensor wells. Sensor material will be applied at these sensor sites which will serve as the analyte detection sensors.

The analyte detection chip depicted in the figure will have 121 sensors. In other embodiments, the analyte detection chip may have fewer than 121 sensors. For example, an analyte detection chip may have two sensor sites, three sensor sites, four sensor sites, or greater number of sensor sites. An analyte detection chip may have two, three, four, five, six, seven, or more sensors sites for sensors. The chip may have ten to twenty, twenty to thirty, thirty to forty, forty to fifty, and fifty to one hundred sensors. A specific embodiment of the analyte detection chip has thirty-two sensor sites. Even more complex analyte detection chips may have many hundreds or thousands of sensors. For example, a chip may have 10,000 sensors (possibly arranged in an array of rows and columns with 100 sensors per side).

The array of sensors may be arranged in many possible formats, and may have an equal number of sensors per side. The arrangement of the plurality of sensor sites is selected as appropriate for a particular application. Although FIG. 2A shows a square array arrangement of sensor sites, the sensor sites may be arranged in any fashion on the chip. For example, the plurality of sensor sites may be arranged in an oblong or rectangular structure, triangular structure, circular or curved structure, and many other arrangements. An array of sensor sites may have 1 site by 10 or more sites, 2 sites by 10 or more sites, 3 sites by 10 or more sites, 10 sites by 20 sites, or 30 by 175 sensors, just to mention some examples. There may also be multiple arrays or multiple groupings of sensor sites on the same substrate. There may be two, three, four, five, or more arrays of sensors on a single substrate.

Figure 2C:
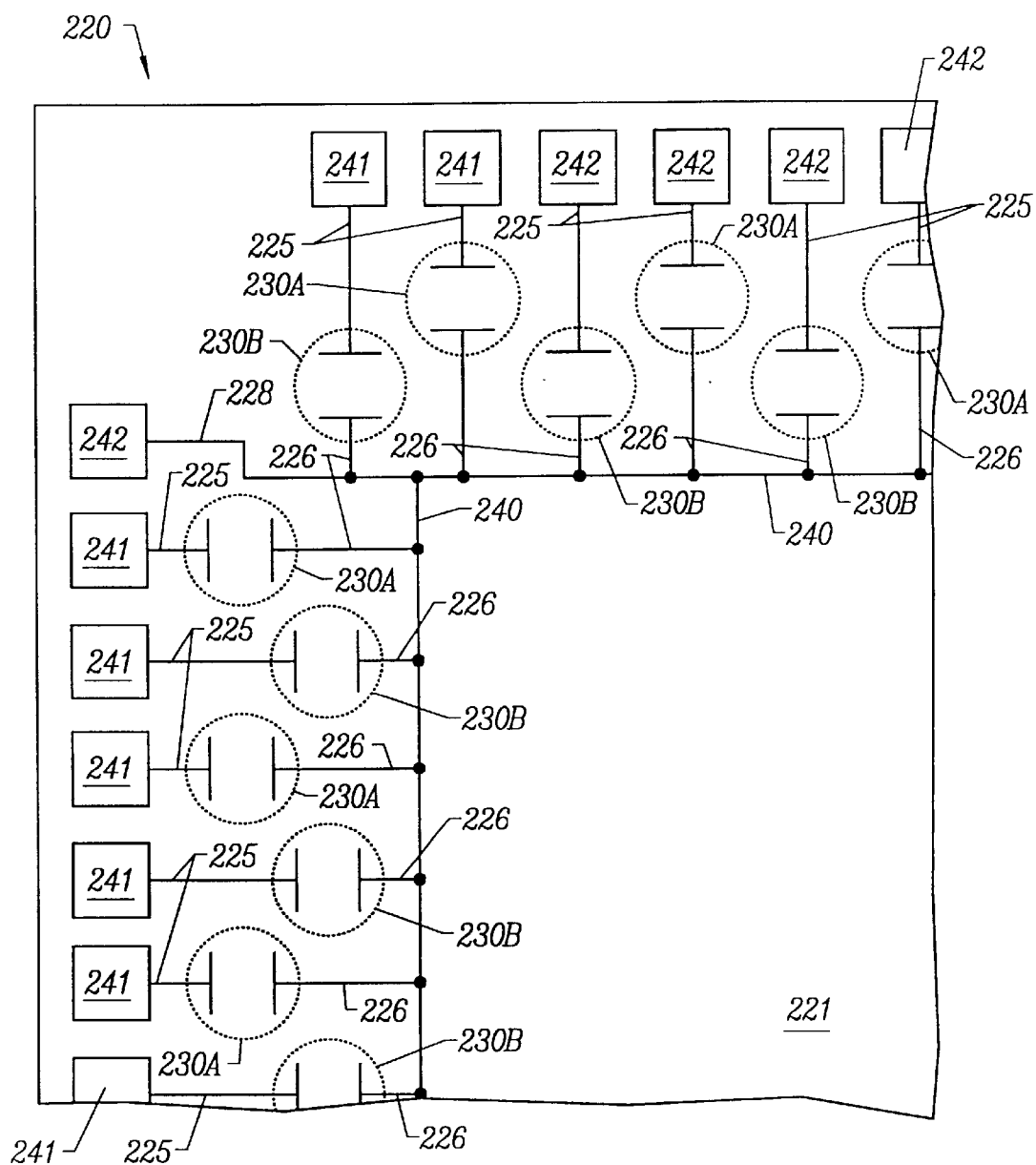
FIG. 2C shows an embodiment of the present invention in which a detection chip is formed with only a single conducting layer.

FIG. 2C illustrates one embodiment of the present invention in which a detection chip 220 is formed with only a single conducting layer formed over a substrate 221. The single conducting layer, typically of metal, such as aluminum and its compounds, advantageously allows for a simple semiconductor process. The simpler processing provides for quicker manufacturing times and a reduced number of failure mechanisms. On the other hand, the simpler processing creates constraints in the layout of the chip 220 and necessarily creates a chip with some functional simplification.

The chip 220 provides for a number of sensors 230A and 230B around the periphery of the substrate 221. Only one corner of the substrate 221 is shown. The sensors 230A and 230B are arranged in two rows and are representationally illustrated by a dotted circle and two spaced apart and parallel line segments. The dotted circle represents sensor material and the two line segments represent the electric terminals by which a reaction of an electrical parameter of the sensor material to an analyte or odorant is received. Each terminal is connected to one of two conductive leads 225 and 226, one lead 226 connected to a common line 240, i.e., a reference line, and the other lead 225 connected to a bonding pad 241. The common line 240 is arranged as a annular ring around the substrate 221 on the inside of the peripheral rows of the sensors 221A and 221B. By a lead connection 228 to a bonding pad 242, the voltage level of the common line 240 is fixed. As seen in FIG. 2C, the two rows of sensors 231A and 231B are arranged in staggered fashion which allows the optimum packing of the sensors. The dotted circle of each sensor 230A and 230B also indicates the possible area covered by the sensor material described previously.

This arrangement permits electrical signals from each sensor 230 through the sensor's bonding pad 241 and the common bonding pad 242. The signals may be derived directly from the electrical characteristics of the sensor material or may be signals which have been preprocessed by the electrical circuits associated with each sensor 230, as described below. In either case, this arrangement can be implemented by "a single-metal layer" process, a term well understood in the semiconductor industry. Processing and layout is advantageously straightforward. With semiconductor technology readily available today, a chip with 32 sensors is easily manufactured. The surface is treated with gold to assure good contacts.

In other embodiments, a system of analyte detection may use sensors that reside on separate substrates. For example, the analyte detection system of the present invention may gather analyte information from sensors in different physical locations such as sensors located at various positions of a production line or different rooms within a building.

Figure 3:
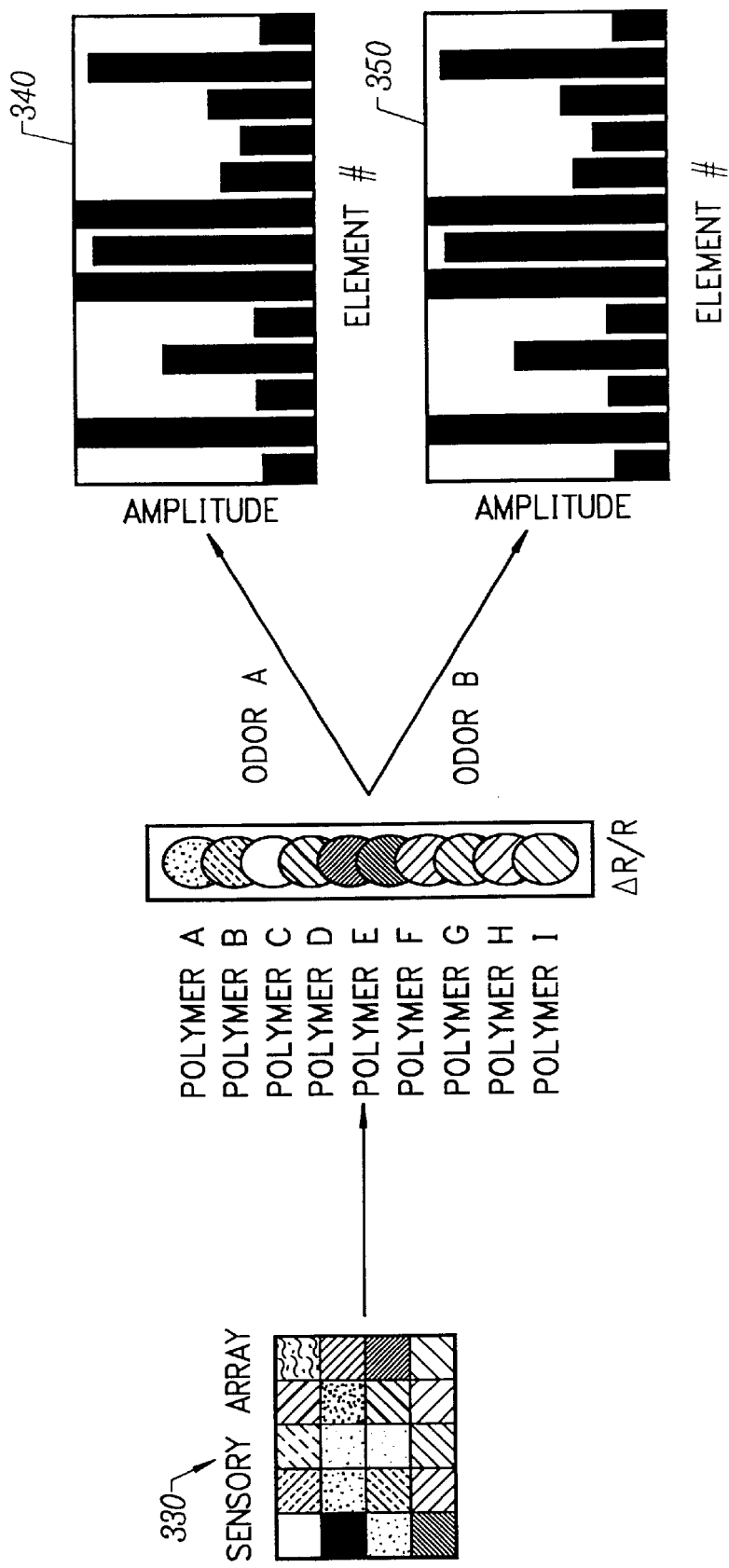
FIG. 3 shows how a sensor array including a collection of different sensors may be used to identify an analyte.

FIG. 3 shows how a plurality of sensors 330 of the present invention is used to identify an analyte. In an embodiment, the sensors are be formed on a substrate at sensor sites, and these sites are arranged in an array form as discussed above. Each of the sensors may be incrementally different, and each is not specifically responsive to any particular analyte. For example, each sensor may have essentially a different polymer composite resistance change (listed as polymer A through polymer I) from every other sensor. When two analytes, such as odor A and odor B, are evaluated using the collection of sensors, the result will be two different response patterns 340 and 350. Each analyte has a characteristic "fingerprint." Pattern recognition processing may then be used to identify the analytes on the basis of these patterns.

In an embodiment of the present invention such as shown in FIG. 3, every sensor has a different composition of sensor material from every other sensor. This may be referred to as "sensor diversity." In other embodiments of the present invention, however, there may be multiple sensors in a sensor array that are the same. In other words, some groups of sensors in this embodiment will be manufactured with exactly the same composition, while other groups of sensors will have a different composition. Having two or more of the same sensors in a sensor array will serve a redundancy purpose, among other purposes, which may be useful to increase the production yield. Redundancy in sensors will also be useful for increasing the service life or reliability of an analyte detection chip, especially when used in harsh environments (e.g., industrial) or mission critical situations (e.g., military, bomb detection, or use by a common carrier). The techniques of the present invention for analyte detection also apply to cases where similar sensors exist in an array of sensors.

An aspect of the present invention is the use of a plurality of sensors having different response characteristics to distinguish and classify analytes. These sensors may be formed on the same substrate. The plurality of sensors will give a multidimensional response for use in characterizing and classifying the analyte.

A particular sensor material may be broadly responsive in the presence of many analytes. A response or signal from one sensor allows detection of a change in the composition of an analyte, but does not necessarily allow identification of that analyte. An array of sensor elements provides a reversible, diagnostic pattern of changes in an electrical parameter (such as resistance, capacitance, or inductance) upon exposure to different analytes. When a number of sensors with diverse chemical compositions is used, an analyte will have a particular fingerprint or signature.

Correlations between the elements of a sensor array may require many more than two sensors to successfully distinguish molecules in a complex environment. A greater number of sensors generally allows the identification of a greater number of analytes. Moreover, a greater number also decreases the chance that two analytes will have a similar or the same fingerprint. The sensitivity of an analyte detection system depends in part on the number of sensors, and diversity of the sensors. The analyte detection system of the present invention may be related to a biological analog, the nose. It is believed the human olfaction system has about $10^6$ total sensors of about $10^3$ different types of receptors. As is well known, dogs have a keener sense of smell than humans. A canine's nose has about $10^8$ sensors, which is two orders of magnitude greater then the human nose.

Greater numbers of sensors are useful in a number of ways. It may be beneficial to measure the same property in many different ways due to noise limitations in a practical system. For example, if sufficient precision could be obtained, it might be possible to identify uniquely any molecule merely from a 38-bit measurement using two sensors. But in practice, it may not practical to make such precise measurements. Hence, when using lower precision measurements, useful information on the nature of the analyte may be obtained by making measurements using many independent determinations from many different sensor elements (such as in a sensor array).

Furthermore, a limited number of sensors may be sufficient to distinguish between a series of pure substances that are maintained at a fixed, known concentration. However, if the background is unknown, if mixtures are present, or if the background gases are changing in concentration, many more sensors may be needed simply to avoid ambiguity in interpretation of the output signal pattern. Even more sensors may be needed if optimal discrimination is to be accomplished between a given target signature and a wide possible range of background clutter. Having large numbers of sensors also allows redundancy and provides the ability to reject or veto the output of poorly performing sensors.

Having greater numbers of sensors are also improve a signal-to-noise response or reduce the time required to identify an analyte. It is possible to achieve signal-to-noise ratio gains from averaging over a large number of sensors during a given observation time. Therefore, with 10,000 sensors, for example, a $n^{1/2}$ signal-to-noise ratio gain would yield an effective sensitivity increase of almost two orders of magnitude over the capabilities of 1 to 10 sensors.

Because of all of these issues, the number of sensors to successfully sense and identify an analyte in a practical device may rapidly multiply from a minimum value. A main goal of array-based sensing is to insure that no two analytes will have the same fingerprint response from the array, and also that a given target pattern is not confused as a mixture of other, unanticipated or unknown, background components. Therefore, it is generally desirable to integrate large numbers of sensors into an array structure. The present invention permits the manufacture of a large number of sensor elements in a low-cost, parallel process. And, the processing allows sensor elements to be chemically diverse.

An array of six to eight sensors is sufficient to adequately distinguish between analytes. This is the case when the electronics used with the sensors provides adequate accuracy, such as a very precise analog-to-digital (A/D)

converter. As the number of sensors increases, fewer bits of accuracy will be required to distinguish between analytes as discussed above. For example, with sixteen to twenty sensors, less precise electronics are needed. With the integrated circuit technology available today, one practical implementation of an analyte detection chip has thirty-two sensors. Signals from thirty-two sensors may be decoded and processed by electronics using an analog-to-digital converter with about twenty bits of accuracy. This is not unduly complicated or prohibitively costly to implement. As integrated circuit technology improves, it is expected that it will become practical to fabricate more than thirty-two sensors on a single integrated circuit, and to process the signals from these sensors.

The chemical sensor material is applied at a sensor site. The chemical sensor material has electrical properties that can be measured in terms of electrical parameters. These parameters may be resistance, capacitance, or inductance. In the presence of an analyte or odor, the chemical sensor material will have a measurable response characteristic. A change or pattern of changes in the electrical properties of the sensors in sensor array may be measured to identify a particular analyte.

By evaluating a change in, for example, the resistance of the sensor material, an analyte detection system of the present invention may identify an analyte. A particular sensor may have a baseline resistance of 50K ohms (R1). However, when the sensor is placed in the presence of an analyte such as water vapor or hexane, the resistance of the sensor may change to 51K ohms (R2). This change in the resistance (i.e., (R1−R2)÷R1) relative to the baseline resistance value may be used to identify the analyte. The baseline resistance value is used as a reference point. The value of baseline resistance may vary depending on the operating conditions of the sensors such as the pressure, temperature, and humidity. The baseline resistance may also vary because the background ambient may change. For example, there may be background analytes which are not of interest and should not be considered during any measurements.

Changes in electrical properties other than resistance of the sensor material may also be measured and similarly analyzed. Resistance has been discussed merely as an example. A change in the capacitance or inductance of the sensor material may be measured to identify an analyte. In the presence of an analyte, the capacitance change of the sensor material (which may be due to a physical swelling of the material) may be measured.

A composition of the sensor material will determine its response characteristic. A sensor in a first position in the array will have a slightly different composition from another sensor in a second position in the array. The two sensors will give different response characteristics, and this difference may be used to help distinguish different analytes or odorants. For example, if a mixture of a nonconductive and conductive polymer is used as the sensor material for an array of sensors, the composition of the sensors may be different. In an embodiment where carbon black is used, the carbon black composition or concentration of each sensor will be slightly different from other sensors in the array.

In addition to the sensor sites for constraining the sensor material, the analyte detection chip of the present invention may include electrical or other connections to the sensor material at the sensor sites. For example, in the case when resistances of the sensors are to be evaluated, conductive layers such as metal are used to connect with the sensor material in a similar fashion as metal interconnect is used in a semiconductor chip. In the case when capacitances are to be evaluated, a conductive material is placed in proximity to the sensor material to allow capacitive coupling and sensing. The electrical signals from the sensor is then routed to bonding pads of the analyte detection chip. Via the bonding pads, the electrical signals from the sensors are connected to off-chip circuitry for further processing and analysis.

Figure 4:
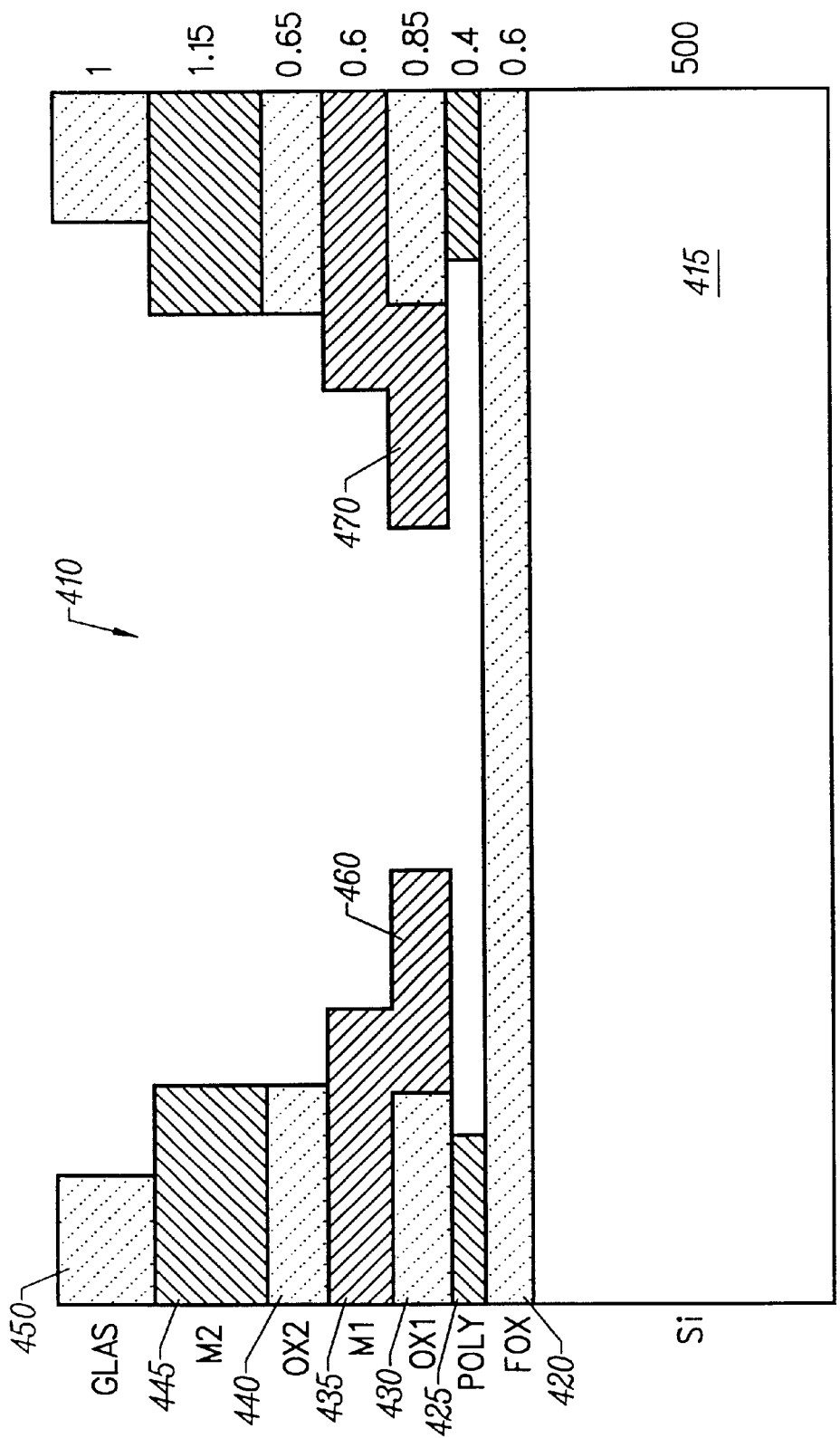
FIG. 4 shows a cross section of a sensor well.

As discussed above, in a specific embodiment of the present invention, sensor wells constrain the sensor material. FIG. 4 shows a cross section of an implementation of a sensor well. This sensor well may be fabricated on a silicon substrate using a CMOS process. The sensor material will fill and be constrained by a sensor well 410. On a silicon substrate 415, the following layers may be patterned and used to form sensor well 410: a field oxide (fox) layer 420, a polysilicon (poly) layer 425, a first oxide (ox1) layer 430, a metal-1 (M1) layer 435, a second oxide (ox2) layer 440, a metal-2 (M2) layer 445, and a passivation or glass (GLAS) layer 450.

An example of a process flow for fabricating a sensor well is as follows. An oxide layer is formed over a silicon substrate. A metal or conductive layer is formed on the oxide layer. The metal layer is patterned and etched. The resulting metal is to be used as contacts for the sensor material. An oxide layer is formed on the structure. A sensor well is patterned and etched. The sensor material is deposited in the sensor well and is in electrical contact with the patterned metal layer.

In one embodiment, the sensor material is applied to the sensor well after the sensor well is formed as a step during the fabrication of the chip (before the formation of the passivation layer). For example, the sensor material is applied at the semiconductor fabrication facility. However, in other embodiments of the present invention, the sensor material may be applied in a postprocessing step, after the fabrication of the chip. For example, the sensor material is applied after the completed wafers are received from the semiconductor fabrication facility.

In one embodiment, the silicon substrate 415 is about 500 microns thick. The field oxide layer 420 is about 0.6 microns thick. The polysilicon layer 425 is about 0.4 microns thick. The first oxide layer 430 is about 0.85 microns thick. The metal-1 layer 435 is about 0.6 microns thick. The second oxide layer 440 is about 0.65 microns thick. The metal-2 layer 445 is about 1.15 microns thick. The passivation layer 350 is about 1 micron thick.

Although the structure in FIG. 4 is fabricated using a two-layer metal process, a sensor well may be fabricated using a single-layer metal process and also processes having more than two layers of metal. For example, a sensor well of the present invention may be fabricated in a process having three, four, five, or more layers of metal.

Electrical connections 460 and 470 are formed in the metal-1 layer to make electrical contact with the sensor material. These electrical connections are used to route the sensor signals to other circuitry for further processing of sensor data. This circuitry may be on-chip or off-chip. The metal conductor used to form connections 460 and 470 is typically a conductive material such as gold, platinum, aluminum, or copper. The material for the electrical connections 460 and 470 should be selected so they are not reactive to the sensor material. In the case when the sensor material is applied during a postprocessing step, connections 460 and 470 will be exposed, and a conductive material such as aluminum may easily oxidize. This may result in poor electrical connections to the sensor material.

Good electrical contacts are more important for some embodiments of the present invention than others. For example, a good physical contact is important when measuring the resistance of the sensor material. This is especially true in cases when the sensor material has a relatively low resistance when compared to the contact resistance. In other cases, such as when measuring capacitance, connections may be made by using a capacitive connection, where there is no physical connection between the sensor material and the conductive material or metal. Consequently, in such an embodiment, there would be fewer concerns associated with oxidation of the metal connection.

The metal-1 layer may be, for example, postprocessed or at least finished in a nonstandard integrated circuit fashion. The surface of standard integrated circuit metalization is normally covered by a thin, air forming, "native" oxide layer. Aluminum, the most popular standard metal, forms aluminum oxide continuously over its surface very quickly when exposed to air. Polymer/carbon black composite resistors can not be taken to high temperatures nor can they be energetically formed in other ways to break through the "native" oxide. As such, a means for good contact to the metal layer must be made. This could be accomplished by chemically or physically etching the exposed electrodes and keeping the metal-1 in an oxygen-free environment while applying the polymer composite sensor material. More practically, an additional layer, or multiple layer sandwich, whose exposed layer is a noble (nonoxidizing) metal may be deposited through any number of techniques on the surface of metal-1. This technique could be physical vapor deposition or chemical vapor deposition or plating amongst others. The technique of sputtering a gold contact layer over a chromium glue layer, followed by photo lithographically defining the metal sandwich is especially attractive.

The circuitry receiving the sensor signals from connections 360 and 370 may be off-chip or on-chip. The other circuitry may include preprocessing, amplification, and classification of the sensor data. Depending on the packaging technology used, bonding pads may be formed along the periphery or edges of the chip, or may be distributed inside the chip (e.g., when using flip-chip packaging technology).

The sensor well structure of FIG. 4 may be used to constrain and allow measurement of the sensor material. The sensor material fills or partially fills sensor well 410, and resistance is measured using electrical connections 460 and 470.

Figure 5:
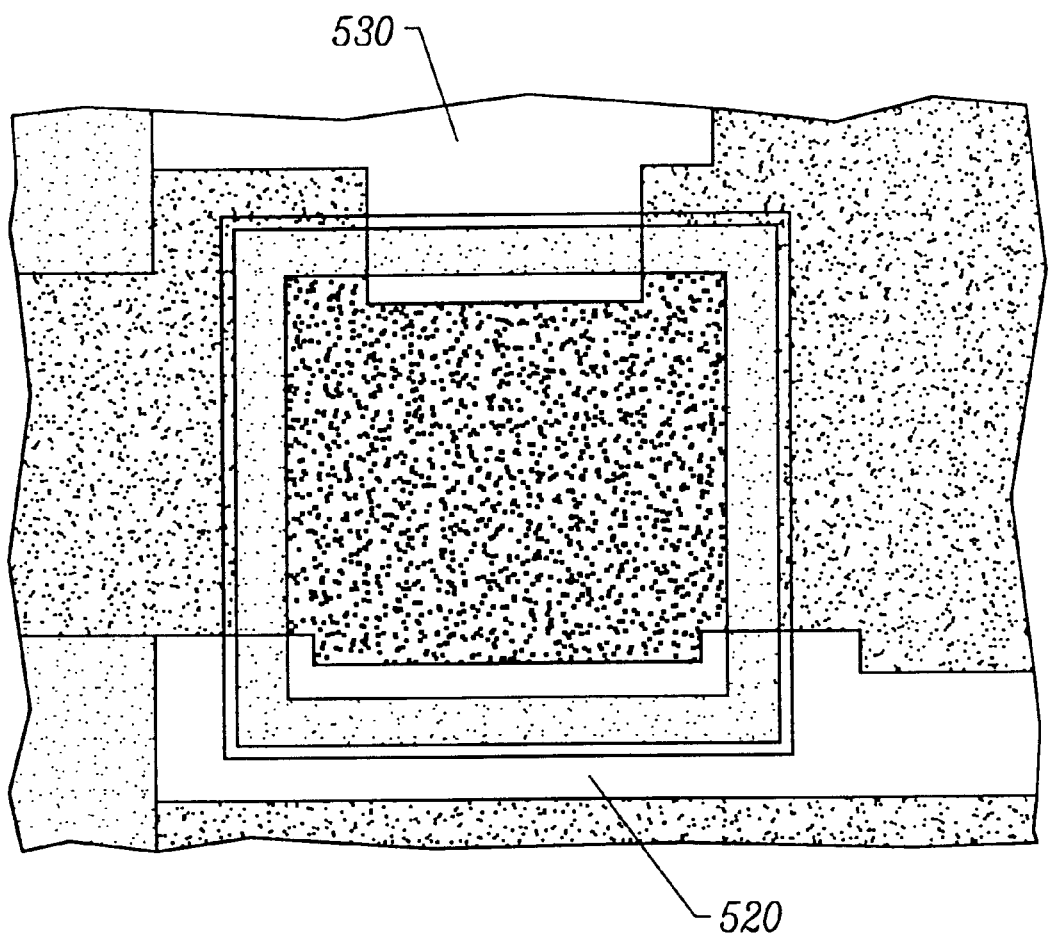
FIG. 5 shows a top view of a layout of a sensor well.

FIG. 5 shows a top view of a 200-micron by 200-micron sensor well structure. Metal is used to make electrical connections 520 and 530 at opposite ends of the sensor well.

Figure 6:
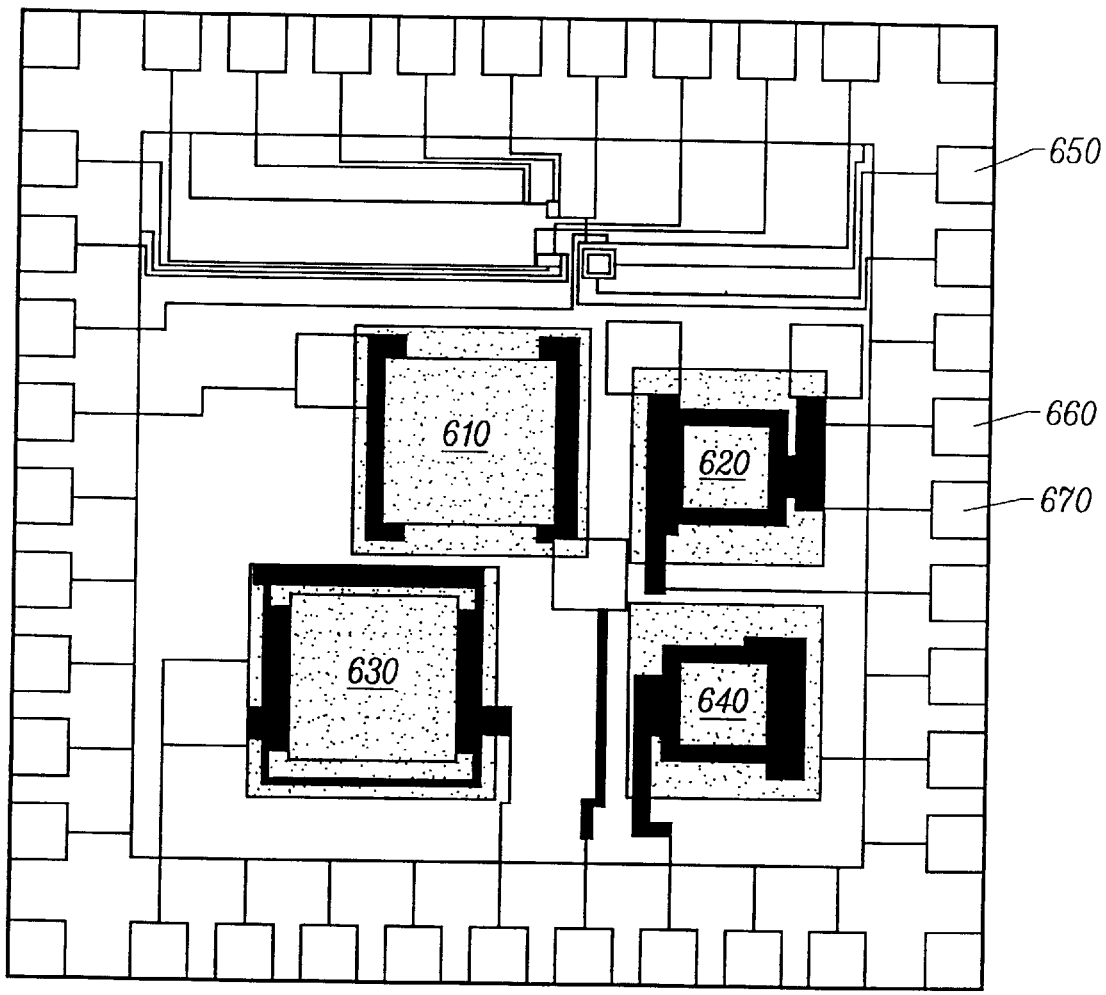
FIG. 6 shows a layout of an integrated circuit with a number of sensor wells.

FIG. 6 shows a layout of a test structure with four sensor wells 610, 620, 630, and 640. These sensor wells are of various sizes. Specifically, sensor wells 620 and 640 are squares of 200 microns per side while sensor wells 610 and 630 are squares of 400 microns per side. Bonding pads 650 surround the four sensor wells and are electrically connected to the sensor wells. Two bonding pads or electrical connections may be used to connect to a particular sensor well. For example, pads 660 and 670 connect to the two terminals for sensor well 620. One bonding pad or electrical connection may be shared between two different sensor wells.

Figure 7:
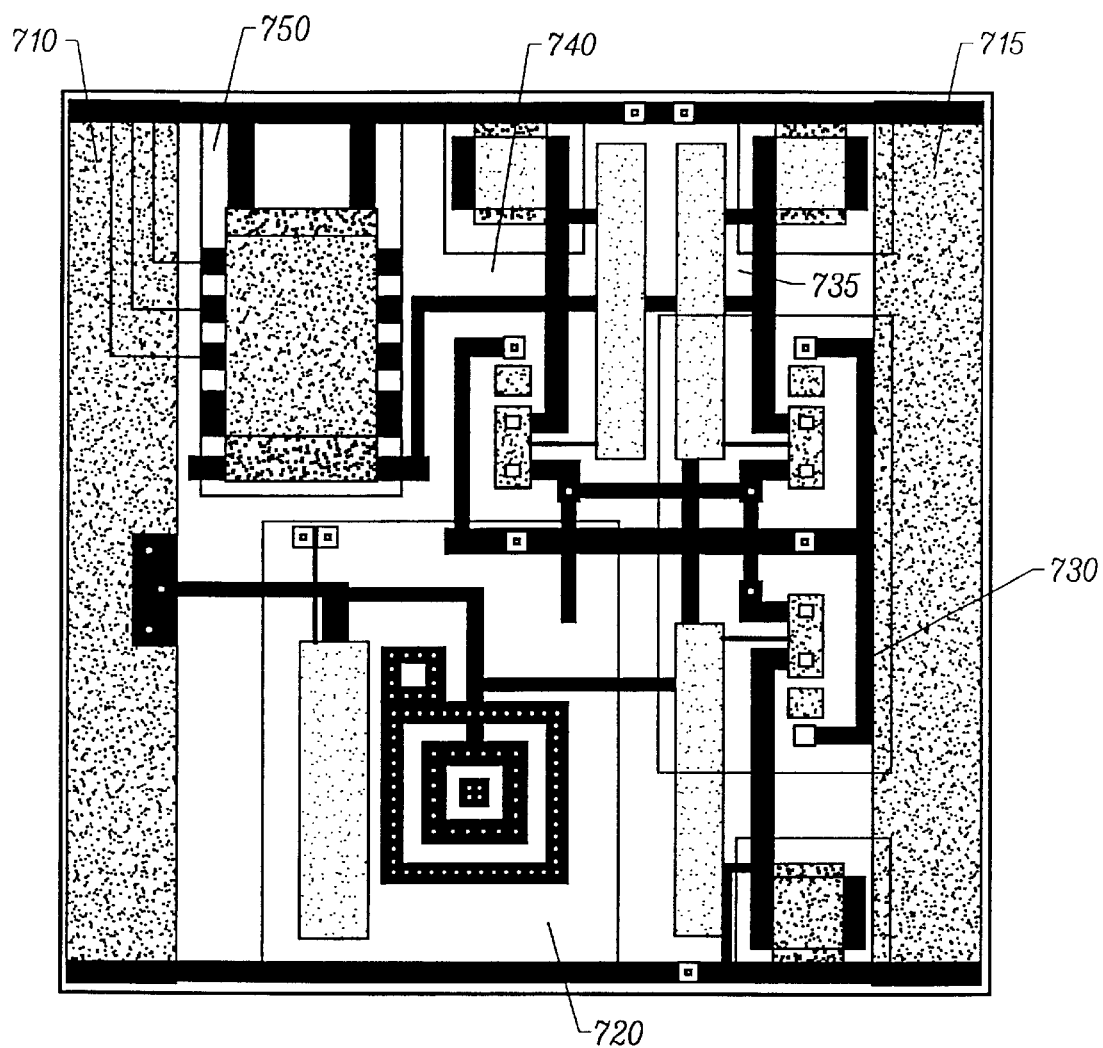
FIG. 7 shows a top view of a layout for a sensor site, where electronic circuitry is formed beneath the sensor site.
Figure 8A:
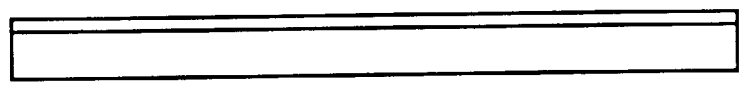
FIGS. 8A through 8F show the different stages in a process of fabricating sensor site and depositing the sensor material.
Figure 8B:
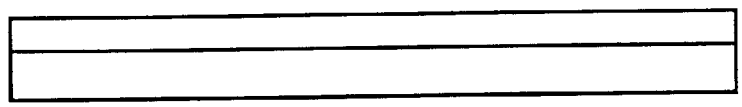
Figure 8C:
Figure 8D:
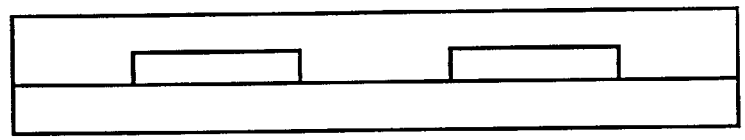
Figure 8E:
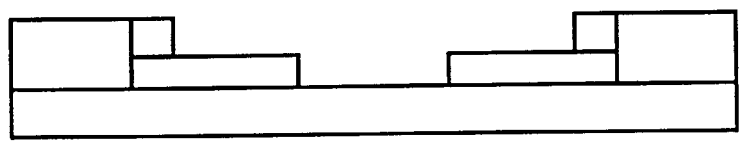
Figure 8F:
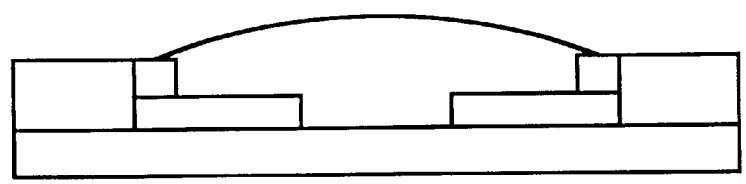

FIG. 7 shows a further embodiment of the present invention where electronic circuitry is formed below or beneath the sensor site. The figure shows a top view of a layout of the electronic devices at a sensor site. Electrical contacts 710 and 715 make electrical contact between the sensor material and electronic circuitry. In this case, the electronic devices implement a preprocessing circuit.

More specifically, the preprocessing circuit may include an autozeroing adaption circuit with signal amplification and X-Y decoding. The individual circuit blocks include a sensor read-out amplifier with baseline adaption circuit 720; signal amplification circuits 730, 735, and 740; and a row/column select and final output amplification circuit 750. In other embodiments of the present invention, however, electronic circuitry for any purpose may be implemented at or beneath the sensor site. Outputs from the electronic circuitry may be routed to other on-chip circuitry, or off-chip circuitry via the bonding pads.

In FIG. 7, the sensor site is a 200-micron by 200-micron sensor well. However, as discussed above, in other embodiments of the present invention, the sensor material may be constrained at the sensor site using a structure or technique other than a sensor well. Furthermore, in other embodiments of the present invention, electronic circuitry is not necessarily formed beneath the sensor site, and may be placed anywhere on the same integrated circuit chip. For example, electronic circuitry is formed adjacent to the sensors, or in another location on the chip. However, an advantage of forming electronic circuitry beneath the sensors is that the resulting layout is relatively compact.

A cross-sectional structure for the embodiment of FIG. 7 will be similar to what is shown in FIG. 4 where the electrical devices are formed using metal-1 and polysilicon layers. To be able to form electrical devices beneath the sensor well, the second oxide layer will not be etched through. The second oxide layer will instead form a "bottom" for the sensor well. The metal-1 layer is used to electrically connect to the sensor material at the sensor site.

FIGS. 8A through 8F show the different stages in the microfabrication a sensor well structure. The technique shown in FIGS. 8A through 8F may be an alternative to a CMOS semiconductor process. For example, the process may be a MEMS or microelectrical fabrication process or other specialized VLSI process. The process may include micromachining to form the structures to constrain the sensor material.

The process can be self-standing (with no underlying electronic circuits) or done in combination with other layers underneath the sequence of layers shown added in FIGS. 8A through 8F. A starting wafer or substrate is shown in 8A. This layer is either an insulating substrate or a starting wafer to which has been added an insulating film. This can be either through oxidation (for a silicon substrate) or deposition. A conductive film may be deposited onto the insulating surface by either physical or chemical vapor deposition methods shown in FIG. 8B. The metal or conductive film is patterned in FIG. 8C leaving a pair of electrodes. An additional insulating film is deposited in FIG. 8D and patterned to expose the electrodes of a nonoxidized metal structure in FIG. 8E. Into the well defined by the top insulator film and between the two electrodes in the bottom of the well, is deposited the sensor material shown in FIG. 8F.

Sensor materials of diverse compositions are applied at the sensor sites of the chip. There are many techniques of applying the sensor material at the sensor sites. For example, the sensor material may be deposited at the sensor sites by using solution spin coating or deposition of monomers and then polymerizing them. In an embodiment where the sensor material are polymer-based chemiresistors, the polymer-based chemiresistors may be formed by spin- or dip-coating substrates with solutions or suspensions of the chemiresistor components. Furthermore, for the case of spin-coated layers or for the case of dip-coated layers, the need for diversity dictates there be a patterning of the first sensor material followed by the application and patterning of many subsequent layers. While not unfeasible, the number of times that this process need be repeated is dictated by the degree of diversity that is desired in the sensors.

Another technique to produce sensor sites containing sensor materials with diverse compositions is to deposit the sensor material serially in time. This will involve making a first deposition at a site which contains a distinct chemical composition from the second, from the third, and so forth.

A still further technique for applying the sensor material is to use microjet or ink jet technology. Ink jet technology is increasingly being used in the fabrication of devices. With such technology, it is possible to fabricate polymeric structures on the order of 100 microns and arrays of these structures with packing densities of greater than 15,000 per square centimeter. Microjets may be useful tools in fabricating large arrays of miniaturized sensors for analyte detection.

For example, to fabricate a diverse set of sensors on a substrate, a continuous jet system may be employed because the composition of the "ink" (e.g., the sensor material which may be a chemical polymer) can be continuously changed. This allows for the fabrication of sensor material films with variable composition from a limited feedstock of monomers or polymers as desired. The monomers delivered into the sensor sites would be polymerized in situ in a subsequent step through exposure to gamma irradiation, to a suitable free radical catalyst or by exposure to light. In this fashion, it will be possible to prepare libraries of thousands of different polymers from uncorrelated monomeric precursors, and to rapidly evaluate their efficacy in distinguishing the analytes of concern.

When using microjet technology, it is important to prevent the ink jet nozzles from clogging. It is desirable for the particle size of the ink be smaller than the nozzle size. In a specific embodiment, microjet technology may be used to apply polymers with carbon black. In fact, classic black inks (such as India ink) are carbon black suspensions. The nozzle size of commercial ink jets is generally greater than ten microns. Since a stable carbon black suspension with particle sizes of less than one micron may be formed, it is possible to fabricate carbon black suspensions compatible with microjet technology.

In addition to standard electrostatically controlled continuous flow or drop-on-demand systems, other options are available. Mechanically controlled ink jets with larger nozzles, essentially small spray guns, may also be used. Another microjet technology is the compound ink jet. With such a device, a jet of the so-called primary fluid emerges from a 10- to 20-micron orifice submerged in a so-called secondary fluid. The resulting jet consists of both fluids, and can be manipulated as in a standard electrostatically controlled continuous ink jet. Compound jets can utilize carbon black based inks, such as India ink, as a secondary fluid since the reservoir for this fluid can be of arbitrary size.

Although the above techniques for manufacturing are highly desirable for some applications, in other applications such as those that include a large numbers of sensor elements in the array, another embodiment of the present invention may be more desirable.

Figure 9:
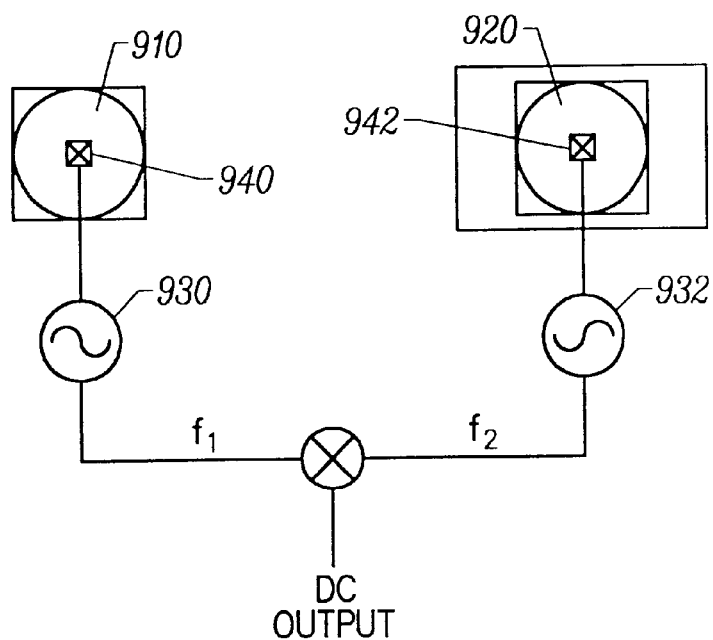
FIG. 9 is a block diagram of a technique for evaluating or measuring the capacitance of a sensor to detect an analyte.

FIG. 9 is a block diagram of an embodiment of the present invention that measures a capacitance of the sensor material to determine the presence of an analyte. While FIG. 9 shows only a single pair of sensors, the circuitry may also be expanded to include an array of sensors or an array of pairs of sensors. Each sensor in the array may include a different type of sensor material from other sensors as described above.

Capacitance is measured in a variety of ways. FIG. 9 depicts one such method. However, other circuitry for measuring capacitance may be substituted for the circuitry shown. In the embodiment shown, two sensors 910 and 920 are provided. Sensors 910 and 920 are sensors formed substantially identical to one another. However, sensor 910 is exposed such that analytes may penetrate the sensor material and cause it to expand. On the other hand, sensor 920 is covered by an insulator layer so that it will not be affected by analytes. As such, sensor 920 is a reference sensor, and its capacitance can be compared with the capacitance of sensor 910 to determine if sensor 920 has expanded due to the presence of an analyte.

One technique of evaluating the capacitors of the sensors involves frequency generators. Frequency generators 930 and 932 are coupled to sensors 910 and 920, respectively, through contacts 940 and 942. Frequency generators 930 and 932 output an oscillating signal at a particular frequency, and receive back return signals f1 and f2. Return signals f1 and f2 may be phase-shifted or frequency shifted, depending upon the capacitance of the sensor. Thus, if sensor 910 has not expanded, the capacitance is the same as that of sensor 920 and f1 is the same as f2. In the case when an analyte is present, the capacitance of sensor 920 is greater, and thus f1 is not the same as f2. In fact, the difference between f1 and f2 may be used to determine the change in capacitance.

The return signals f1 and f2 are input to a discriminator mixer 950. Discriminator mixers are well known in the electrical arts, and in particular for example, in the design of phase locked loops. Mixer 950 receives two frequencies, and outputs a DC output that is zero if the frequencies are the same, and nonzero if the frequencies are different. The greater the frequency difference, the higher the value of the DC output. Thus, if the output of mixer 950 is zero, then the capacitance of the two sensors are the same, and no analyte is present; if the magnitude of the output is nonzero, then an analyte is present, and may be identified by the value of the DC output.

Of course, other capacitance measuring circuitry may also be used. For example, two similar adjacent sensors may be formed such that they have room to expand in a sideways direction. Each of the two sensors are coupled to a different conductive trace, and the sensors are coupled through the conductive trace to a capacitance measuring circuit. When no analyte is present, the sensors have a certain separation, that is known, and thus has a known capacitance. When an analyte is present, the sensors expand and the distance between them shortens causing the capacitance to change. By measuring the change in capacitance, the presence of the analyte may be determined.

Figure 10:
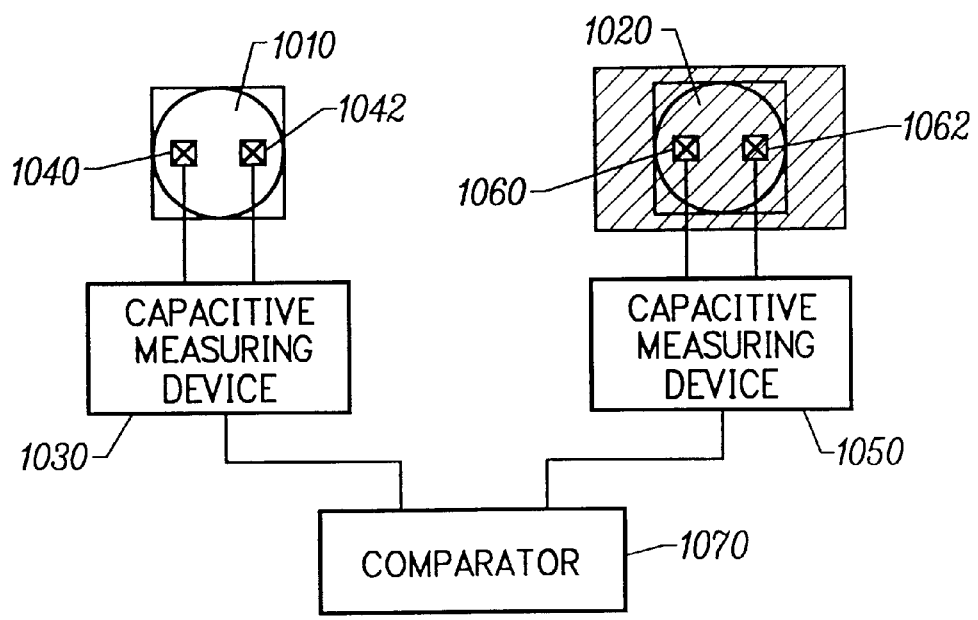
FIG. 10 shows another embodiment for evaluating or measuring the capacitance of a sensor element.

FIG. 10 shows another embodiment of the present invention for measuring the capacitance of a sensor element. Two similar sensors 1010 and 1020 are provided. In a specific embodiment, sensors 1010 and 1020 are substantially identical. A capacitive measuring device 1030 coupled to sensor 1010 by two conductors 1040 and 1042 through contacts or otherwise. The capacitive measuring device is any device capable of determining a capacitance of sensor 1010. Similarly, a second capacitance measuring device is coupled to sensor 1020 through two conductors 1060 and 1062. Sensor 1020 is isolated from exposure to analytes, while sensor 1010 may be exposed to them. A comparator 1070 compares the capacitances measured from the two sensors 1010 and 1020. These values may be analyzed by various techniques described above or otherwise.

Figure 11:
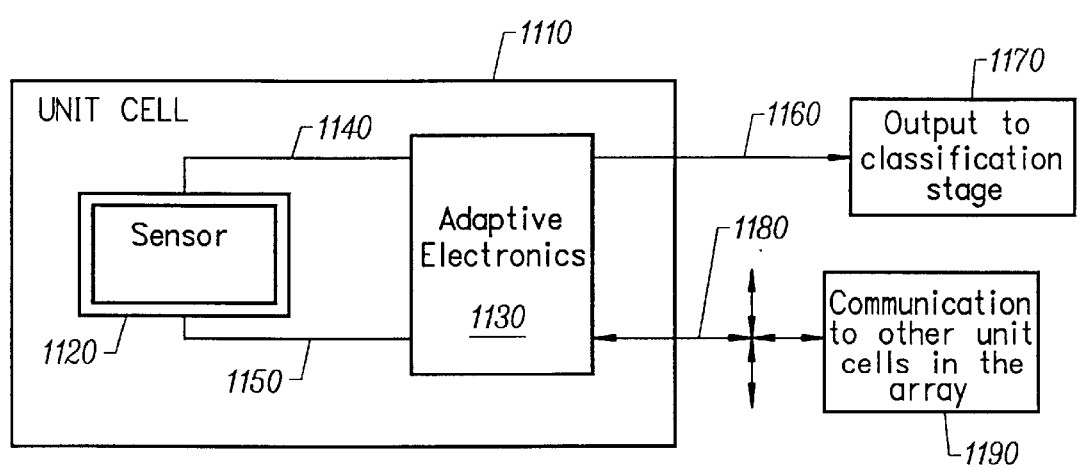
FIG. 11 shows a unit cell.

FIG. 11 shows a "unit cell" 1110 for a sensor of the analyte detection chip of the present invention. To form a plurality of sensors, unit cell 1110 is repeated as many times as desired. For example, for an analyte detection chip with ten sensors, the unit cell is repeated ten times. For an analyte detection chip with thirty sensors, the unit cell is repeated thirty times. For a chip with one hundred sensors, the unit cell is repeated one hundred times. For a chip with "n" sensors, the unit cell is repeated at least "n" times.

As discussed above, a basic embodiment of unit cell 1110 includes sensor 1120 by itself. Electrical connections from the unit cell will be connected to other circuitry, on-chip or off-chip, for further processing. For example, in a two-chip analyte detection chipset solution, a first of the chips will contain a plurality of sensors 1120 and their respective electrical connections. A second of the chips will be electrically coupled to sensors 1120 to process the signals from the sensors on the first chip.

A more highly integrated embodiment of unit cell 1120 includes sensor 1120 and adaptive electronics 1130, both on the same chip or substrate. Adaptive electronics 1130 may be formed beneath the sensor site of sensor 1120, as was described for FIG. 6 above. The adaptive electronics 930 are electrically coupled to sensor 1120 by connections 1140 and 1150. The adaptive electronics may use adaptive signal processing techniques to tune out the environment background.

In one embodiment, the unit cell includes the sensor that is coupled to the adaptive electronics. The adaptive electronics compensates for baseline drift, and provides normalized gain. An output of the unit cell will be an effective normalized percentage change for this sensor relative to the array of sensors. The adaptive electronics may communicate with other cells in the array via signal lines or a resistive grid network (discussed further below). The communication network may facilitate both the reception and transmission of the analog information needed for adaptive gain setting and normalization.

The adaptive electronics provides an output 1160 that may be used to further process and analyze the data generated by the sensor. For example, in the embodiment of FIG. 11, output 1160 is coupled to a classification stage 1170 for classification of the odor or analyte input to the sensor. This classification stage may include a computer and software running on this computer. In another embodiment, signals on output 1160 may be used to control a mobile device to trace or track an analyte plume to its source.

The circuitry or electronics that output 1160 is connected to may be on-chip or off-chip. For example, output 1160 may be connected via a network (e.g., local area network, wide area network, intranet, or the internet) to a remote computer. Output 1160 may be used by on-chip circuitry such as an on-chip microcontroller or microprocessor, signal processing unit, neural network processing circuitry, and other on-chip circuits.

Unit cell 1110 may be connected to other unit cells 1190 in an array or group of unit cells via connections 1180. Connections 1180 permit communication between the unit cells. Communication between the unit cells may permit higher performance of processing of the received sensor data.

Figure 12:
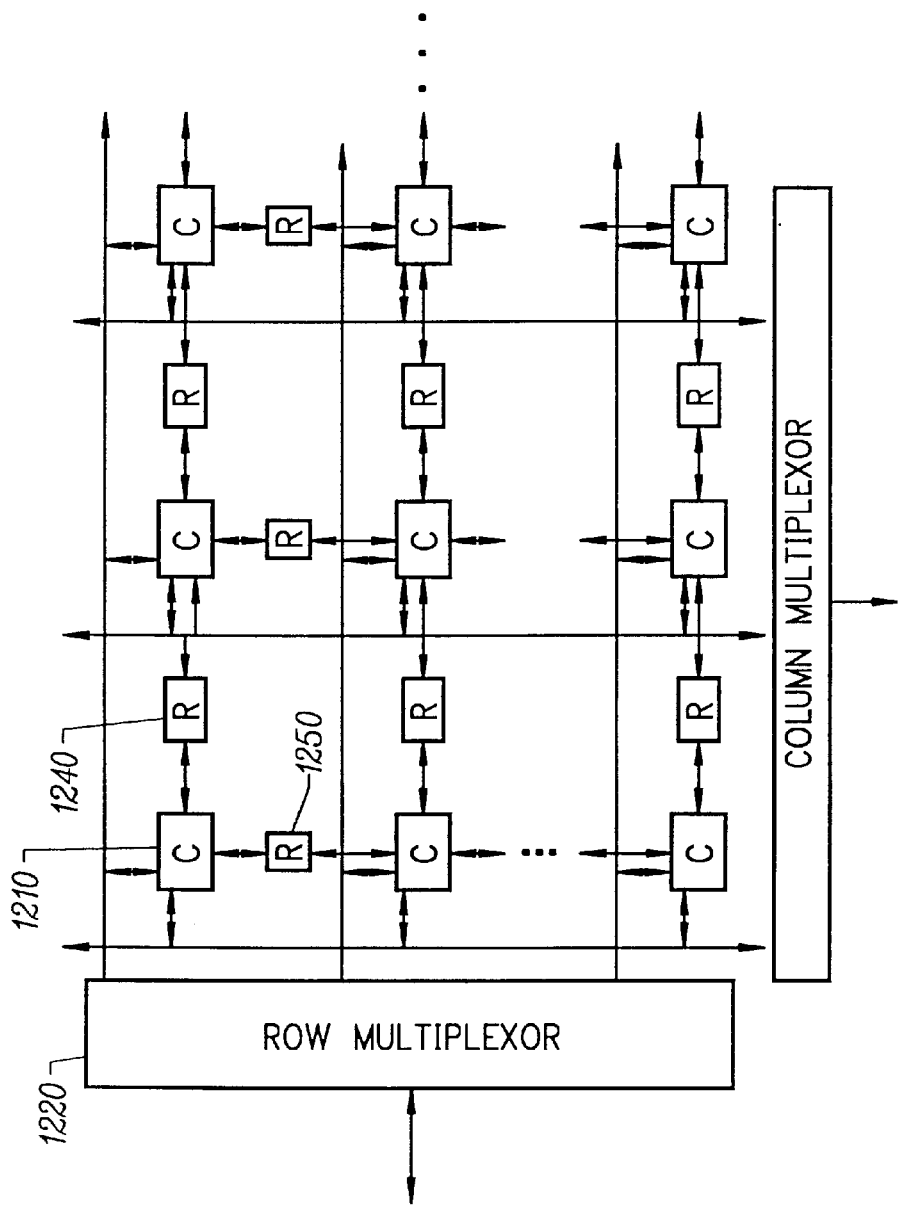
FIG. 12 shows a diagram of an array of analyte detection sensors.

FIG. 12 shows a diagram of an array of sensors 1210 of the present invention. Each of these sensors may be implemented using a unit cell 1110 as described above and shown in FIG. 11. In FIG. 12, the sensors are arranged in rows and columns. However, other arrangements of sensors are possible. The array may be of any desired size.

In the embodiment of FIG. 12, the rows of sensors are "addressed" by a row multiplexer 1220. The row multiplexer selects a particular row in the array of sensors. For example, based on a row address input to the row multiplexer, a corresponding row will be selected. There will be a unique row address for each row in the array of sensors. Similarly, the columns of sensors are addressed by a column multiplexer 1230.

The address input to the row and column multiplexer may be held in a register, counter, shift register, random access memory, or other storage device. For example, to cycle the columns in the array of sensors, a counter is repeatedly incremented or decremented until all the columns have been addressed. Or, if a shift register is used, a particular bit or set of bits will be repeatedly shifted.

Data from the sensors of the selected row or column may be output in serial or in parallel. For example, data from a plurality of sensors is shifted out from the column multiplexer as a plurality of serial signals. The signals may be frequency, time, code or otherwise multiplexed. Sensor data can also be output in parallel signals from multiple columns at the same time. Each of the parallel signals may be frequency, time, code, or otherwise multiplexed. The outputs of the multiplexers may be analog signals. The outputs may also be digital signals such as an embodiment where each unit cell includes some analog-to-digital conversion. The outputs of the multiplexers may include both analog and digital signals.

In the embodiment of FIG. 12, sensor 1210 is coupled to communicate to adjacent sensors as discussed in FIG. 11 above. Specifically, sensor 1210 is coupled through a resistor 1240 to an adjacent sensor or sensors in the same row. Sensor 1210 is coupled through a resistor 1250 to an adjacent sensor or sensors in the same column. Effectively, the array of sensors will communicate with each other through a resistive grid.

Resistors 1240 and 1250 may be formed using the inherent resistance of the wiring (e.g., parasitic or unintentional resistance) between the sensors. Resistors 1240 and 1250 may also be implemented using one of the many other techniques used to obtain resistance on an integrated circuit such as forming a diffusion or polysilicon resistor, or using a transistor.

Through resistors 1240 and 1250, a sensor cell in a center location of the array will be connected to two adjacent sensor cells in a row above and below it, and to two adjacent sensor cells in a column to the left and right of it. Similarly, a sensor cell in the first row or last row edge of the array will be connected to one adjacent sensor cell in a row above or below it, and to two adjacent sensor cells in a column to the left and right of it. A sensor cell in the first row or last column edge of the array will be connected to two adjacent sensor cells in a row above or below it, and to one adjacent sensor cell in a column to the left and right of it. A sensor cell in a corner of the array will be connected to one adjacent sensor cell in a row above or below it, and to one adjacent sensor cell in a column to the left or right of it.

The resistive network provides an intercell communications architecture that also permits adaptation and filtering to be performed in parallel in an efficient manner. The resistive grid allows the implementation of local spatial averaging between sensors. By controlling resistance values within the network, the spatial extent of this averaging can be controlled. Furthermore, it provides a means of weighting the averaged signals based upon distance in the array. Modifying the resistance values based upon signal input values allows the circuit to dynamically change signal averaging weights and spatial averaging extent. Thus, for relatively weak signals, it is possible to increase local spatial-weighted averaging. In this situation, the ability to localize and track the analyte is reduced, but the detection limit of weak analytes is significantly improved. Conversely, for stronger analytes, the amount of averaging might be dynamically reduced, greatly enhancing the ability to localize the smell and provide analyte tracking information. Thus, performance is improved in all signal level environments.

The use of a resistive network also facilitates the implementation of preferential response increases with analyte concentration increases. The analyte detection system may encode analyte intensity information by having analyte detection cells with different activity level thresholds. As the analyte concentrations increase, more cells with higher activation levels are included in the output response. By utilizing a resistive network that controls the amount of local spatial averaging, a means of incorporating the outputs of sensors with higher activity thresholds as well as protecting against damaged sensors which may indicate high concentration activity due to sensor fault is provided.

The resistive grid can implement both linear and nonlinear filtering. The resistive grid may also incorporate dynamic response by the introduction of memory such as a capacitive memory at the nodes. Thus, very complex temporal and spatial signal processing can be implemented in a very efficient manner. In addition, multiple resistive grids can be overlaid in the architecture. One grid could communicate and filter gains among the unit cells, while another grid communicates baseline settings. In this manner the resistive grid architecture can be used to perform efficient normalization across the array in a parallel adaptive manner.

In an embodiment of an array of sensor cells, there may also be dummy rows and columns of sensors, which is a row or column of sensors is formed but not used functionally as are active rows and columns of sensors. For example, at row and column edges of the array, dummy rows and columns of sensors may be formed. These dummy rows and columns of sensors may be used to ensure the active interior row and columns of sensors are relatively uniform, since sensors at the edge may exhibit some edge effects by not having a similar number of adjacent sensors as for the interior sensors.

Dummy row and columns (not necessarily at edges of the array) may also be used in a redundancy scheme when these are activated, possibly by laser programming or programming of nonvolatile or one-time programmable memory elements such as Flash, EEPROM, EPROM, or antifuse cells. These dummy row and columns may be used in the place of other rows and columns that are or have become defective. For example, a redundancy scheme may help improve the yield of good die, or increase the service life of an analyte detection chip. The preprocessing circuitry evaluates changes in the chemical sensors. The chemical sensors used in the analyte detection system exhibit a change in resistance when exposed to the analyte for which they are specifically tuned. It is not a straightforward procedure to directly measure a change in resistance using an analog circuit. However, circuits can be made which will respond to a change in voltage or current. And, by Ohm's law (i.e., V=I*R), a change in resistance (R) may be measured by keeping either the voltage (V) or current (I) constant. Then, the change in resistance may be determined by measuring a change in the other variable. For example, if the current is kept constant, any change in resistance will cause a directly proportional change in voltage. And, if the voltage is kept constant, the current will change inversely proportional to the change in resistance.

The preprocessing or adaptive circuitry may use either the constant current or constant voltage approaches. Additionally, a circuit that uses an autozeroing approach is discussed below. These circuits adapt out slow changes in sensor resistance due to changes in humidity or temperature and provide an adjustable means of removing the low frequency elements of the signal in order to focus on faster analyte concentration changes. In addition, the circuitry will adapt out the long-term presence of an analyte, much like a biological system grows accustomed to the presence of an analyte. These circuits will produce voltage, current, or pulse train outputs suitable for input to the classification hardware, or for off-chip communication.

A voltage mode circuit gives a current out-put proportional to a change in the sensor resistance over a period of time determined by the follower bias and the capacitance on the follower output. The circuit attempts to keep the voltage across the sensor constant, while measuring the change in current.

Figure 13:
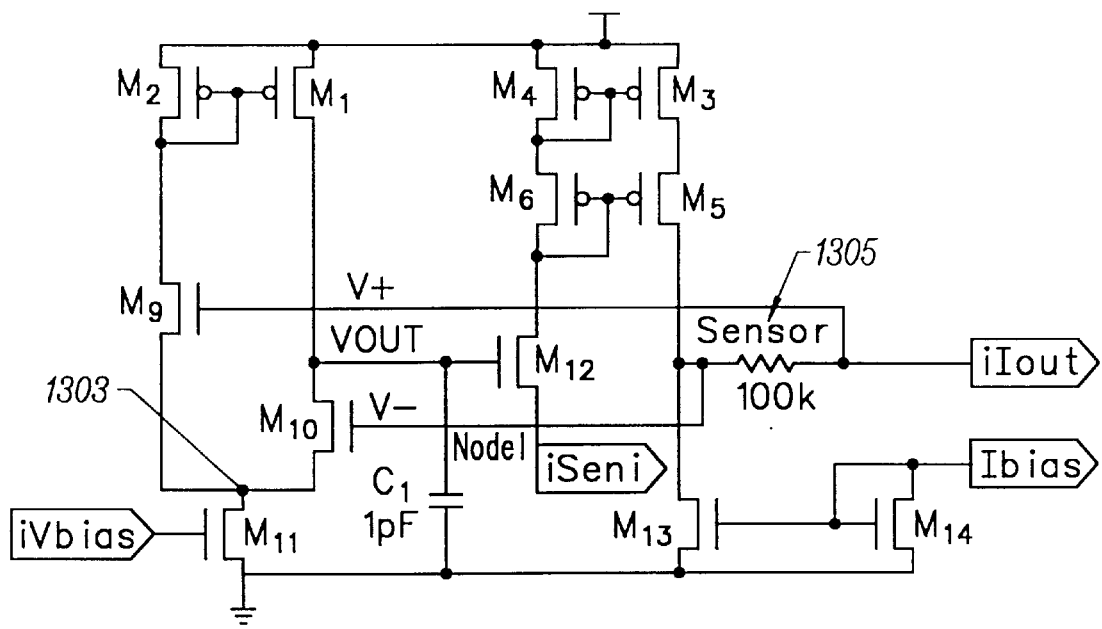
FIG. 13 shows electronic circuitry for adaptive preprocessing using a constant current bias.

The circuit shown in FIG. 13 uses a constant current bias on sensor 1305. Transistors M2 and M9 are coupled between VDD and a node 1303. A gate of M2 is coupled to a source of M2. A gate of M9 is coupled to a first terminal (i.e., V+) of a sensor 1305. The first terminal of sensor 1305 is also coupled to a node iIout. A transistor M11 is coupled between node 1303 and ground, and has a gate coupled to iVbias.

A transistor M1 is coupled between VDD and a Vout node, and has a gate coupled to the gate of M2. A transistor M10 is coupled between Vout and node 1303, and has a gate coupled to a second terminal (i.e., V-) of sensor 1105. A capacitor C1 is coupled between the Vout and VSS.

Transistors M4, M6, and M12 are coupled between VDD and Node1. A gate of transistor M4 is coupled to its drain. Similarly, a gate of transistor M6 is coupled to its drain. A gate of transistor M12 is coupled to Vout.

Transistors M3 and M5 are coupled between VDD and the second terminal of sensor 1305. A gate of transistor M3 is coupled to a gate of M4, and a gate of transistor M5 is coupled to a gate of M6. A transistor M13 is coupled between the second terminal of sensor 1105 and VSS, and has a gate coupled to an Ibias node. A transistor M14 is coupled between Ibias and ground. A gate of transistor M14 is also coupled to Ibias.

The preprocessing circuitry or adaptive electronics in FIG. 13 for a sensor adjusts for baseline drift. The voltage is maintained by a feedback circuit that keeps the voltage across the sensor so the current in the sensor is equal to a reference current. If analyte molecules diffuse into the sensor material and cause a change in resistance, a delta R will be reflected in a change in the current through the sensor since I is held constant. Thus, a difference between the reference current and the bias current may be determined or computed. Specifically, this difference may be easily computed in analog circuitry with a few transistors. If the bias current is the same for all sensors, then a normalized change in resistance may be achieved with relatively little hardware.

This difference in current can be used directly as output. However, a neuromorphically inspired processing method is to input the current to a pulse neuron circuit which then outputs the change as a series of pulse trains, similar to the way the biological systems encodes information. This representation may be useful when considering large arrays of sensors, and is addressed in more detail later. The adaptation circuit may be set to respond quickly, which is why the spike train frequency diminishes. In effect, the circuit is "getting used" to the analyte. This is valuable as the real information is contained in the change in the analyte concentration. Once the circuitry has determined what analyte is present, it is not necessary to use energy and bandwidth in communicating that the analyte is present, only if this analyte gets stronger or weaker.

Figure 14:
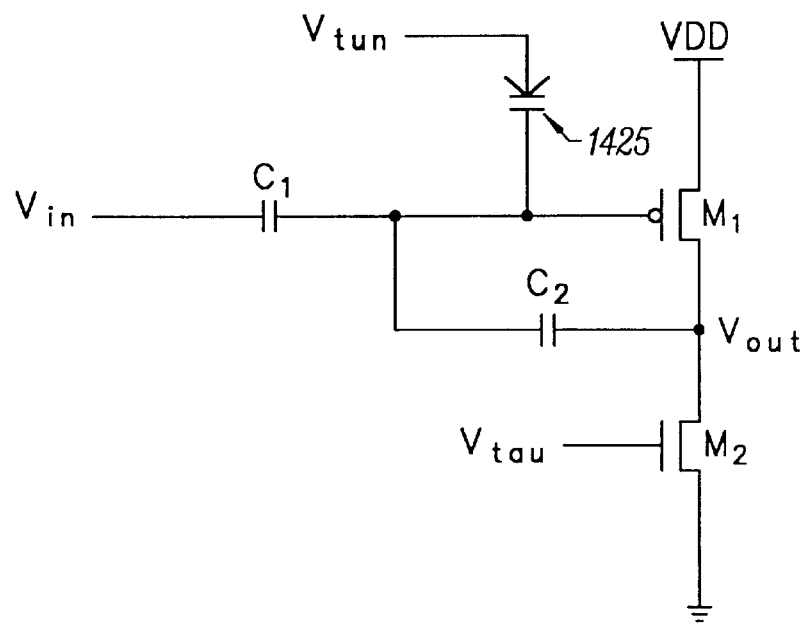
FIG. 14 shows electronic circuitry for preprocessing.

FIG. 14 shows an autozeroing amplifier that automatically adapts out the DC value of the input. This amplifier may be a useful building block for integrated circuits having a plurality of sensors that are to be normalized, such as an analyte detection chip. This two-transistor circuit continuously nulls any DC offset but still allows signals as slow as 0.1 Hz to pass unimpeded.

A PMOS transistor M1 and NMOS transistor M2 are coupled in series between VDD and VSS supplies. A Vout node is between the M1 and M2 transistors. A gate of M2 is coupled to a Vtau bias voltage input. A Vin input is coupled via a capacitor C1 to a gate of M1. A capacitor C2 is coupled between the gate of M1 and the Vout node. A floating gate device 1425 is coupled between a Vtun input and the gate of M1. Floating gate device 1425 may be, a floating gate transistor or pFET device for example.

The gain of this amplifier is determined by the ratio of −C1/C2. And, a corner frequency of the amplifier is set by the bias voltage applied at Vtau.

Floating gate device 1425 is provided as a memory or storage element. According to this embodiment, there would be one memory element associated with each sensor on the analyte detection chip. Floating gate device 1425 provides nonvolatile storage. Other memory or storage elements may be used in the practice of this invention including dynamic-type memories, RAM memories, Flash cells, EEPROM cells, EPROM cells, registers, counters, flip-flops, and many others.

In the embodiment in FIG. 14, floating gate device 1425 is fabricated using a standard CMOS process and can store an analog value with about 14 bits or greater of accuracy. The floating gate device may store analog values with fewer than 14 bits accuracy. Floating gate device 1425 may be referred to as an "analog memory cell." This is in contrast to a digital memory cell, which stores ones and zeros.

For an analog memory cell, an amount of charge is stored on a floating gate of the floating gate device that is representative of the analog value. In other words, a threshold voltage (VT) property of the floating gate device is altered to store an analog value. The advantage of using an analog memory cell such as floating gate device 1425 is that it requires only about the space of a single transistor. The floating gate device requires no power to retain its memory, does not require refreshing, and requires no special fabrication techniques. Such circuitry may be used in the implementation of an analyte detection system to provide for adaptation and learning.

Current-mode circuits using floating gate MOS transistors operating in their subthreshold regime may produce as output currents products or quotients, or both, of powers of the input currents. The circuits capitalize on the exponential current/voltage relationship of the subthreshold MOS transistor and the voltage summation afforded by a capacitive divider. The power law relationships are set by capacitor ratios, and hence, can be quite precise. The quantity of charge stored on the floating gates in one of these circuits sets an electronically modifiable, nonvolatile scale factor for the product relationships which can be used to compensate for device mismatch or as weights in a variety of analog neural network implementations. These circuits offer a mechanism for dealing with sensor mismatch in the absolute magnitudes of baseline resistances and signal changes upon analyte detection of the sensor array.

In addition to long-term storage, floating gate technology has another advantage in that the mechanisms operate on a very large time-scale. This is important since on VLSI chips, long time-constants may sometimes be difficult to realize due to the relatively small size of on-chip capacitors. Floating gate technology allows the realization of time constants from milliseconds to days.

Figure 15:
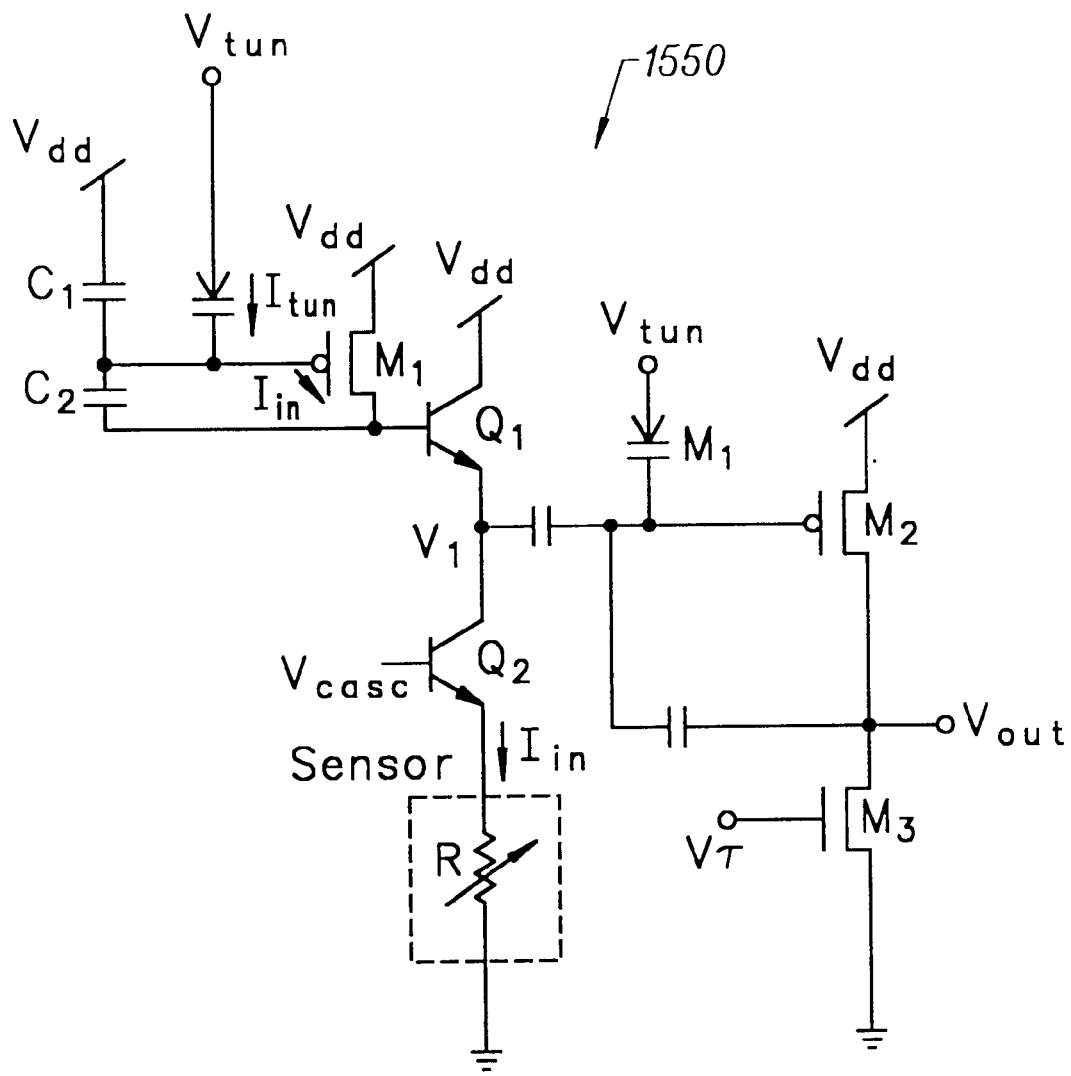
FIG. 15 shows electronic circuitry for preprocessing including an autozeroing amplifier.

FIG. 15 shows a further embodiment of an autozeroing amplifier of the present invention. This amplifier configuration shares some similarities to that in FIG. 14. The sensor circuit in FIG. 15 has two stages. The first stage includes a floating gate device 1550 (e.g., floating gate pFET) and two NPN transistors Q1 and Q2. The NPN transistors are used as current amplifiers so that the floating gate device can operate below threshold. The capacitive divider formed by C1 and C2 results in a weaker exponential relationship in the floating device, resulting in a large voltage swing for a given change in source current. The largest voltage change occurs when C2 is only the overlap capacitance from floating gate to drain. Transistor Q2 acts as a cascode to the resistive sensor to increase the amplifier gain.

The second stage is an autozeroing floating gate amplifier to amplify the output of the first stage. For example, a bandpass gain may be approximately 52 decibels, which results in a 5-volt output voltage change for a one percent resistance change. A floating-gate device M1 (e.g., pFET transistor) of the second stage is an integral part of the sensor operation. Hot electron injection is used to add electrons to the floating gate, and Fowler-Nordheim tunneling is used to remove electrons from the floating gate. The tunneling junction is treated as a constant current source. Hot electron injection occurs when electrons have enough energy to cross the 3.1 electron-volt barrier created by the gate oxide. In a pFET, holes are the majority carrier and electrons are formed during impact ionization in the drain depletion region. This process generates electrons for hot electron injection.

In a steady state, the sensor is at its quiescent resistance. The currents through Q1 and Q2 are balanced, giving a quiescent output voltage. The gate of M1 is held stable by the balance of tunneling and injection currents. When a analyte is detected, the resistance of the sensor increases, reducing the current in Q2, causing V1 to increase. As a result, the drain-to channel voltage in the pFET decreases, which in turn reduces injection. The tunneling current is then greater than the injection current and causes the output voltage to adapt back to its quiescent value. Adaptation occurs slowly because the hot-electron-injection and tunneling currents are several orders of magnitude smaller than the quiescent pFET source current.

The first stage amplifier has a typical bandpass filter response with a low frequency cutoff at $2\pi/\tau$ which can range from about one hertz (or lower) to the megahertz range. It is also important to note that the gain is determined by a ratio of capacitors C1/C2, which are shown to match well in VLSI processes. The Q2 and M1 are designed so the open-loop gain is much larger than the closed-loop gain provided by the capacitors.

The first stage amplifier provides gain and transduces a resistive change into a voltage change rather than amplifying a voltage change. In addition, the sensor circuit normalizes the output from the sensor due to the circuit's logarithmic response and to the sensor's percentage change property. This allows for long time-constants similar to those observed in biological olfaction systems.

An adaptive winner-take-all circuit may also be used in the analyte detection chip of the present invention. The traditional winner-take-all circuit takes an array of inputs and has an output that represents the location and magnitude of just the largest input. A winner-take-all circuit may be implemented using floating gate devices and will have little physical size increase over classical circuitry. An adaptive version of this circuitry slowly nulls the inputs over time. This results in an output that responds to changes in the input regardless of the steady-state input magnitudes. Such a circuit has application in the sensor array for suppression of noise and faulty sensors.

Figure 16:
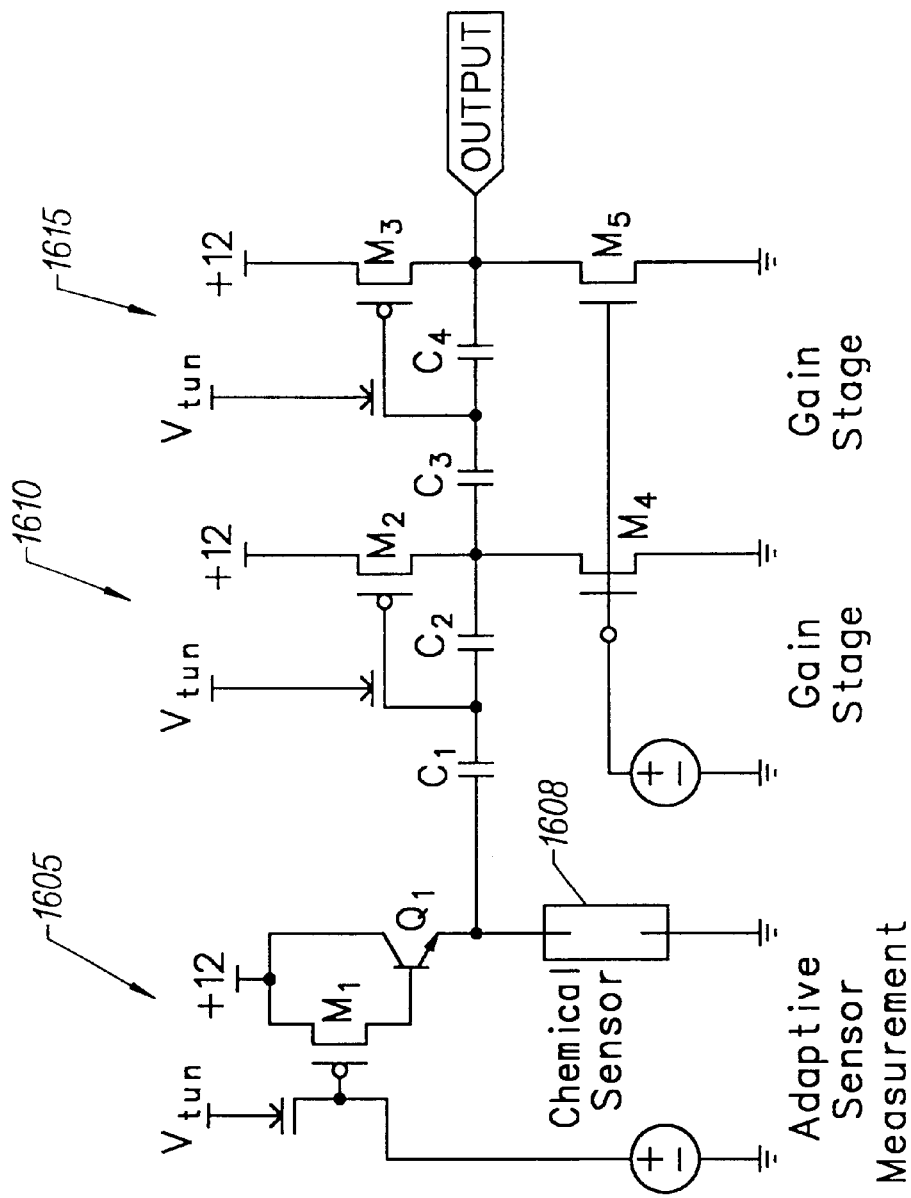
FIG. 16 shows electronic circuitry for sensor preprocessing based on an autozeroing amplifier.

FIG. 16 shows a circuit for sensor preprocessing based on the autozeroing amplifier. The circuit performs adaptation, resistance sensing, and gain with very few transistors and exploits the physics of the MOS transistor to perform these computations in relatively little silicon area. An adaptive sensor measurement circuit 1605 produces an output proportional to the percentage change in resistance of chemical sensor 1608. Gain stages 1610 and 1615 are added to increase the sensitivity. The gain or amplification stages 1610 and 1615 are similar to that discussed above and shown in FIGS. 13–15. The circuit also adapts out changes in the sensors and circuitry on an adjustable time scale.

A layout of the circuitry shown in FIG. 16 is shown in FIG. 7. As was described above, FIG. 7 shows an example of the layout of the preprocessing circuitry as it would be placed in a space beneath the sensor site. The layout is for a standard CMOS process and includes X-Y decoding circuit 750 for an array implementation. Contacts for 710 and 715 are to the on-chip sensor deposition. Sensor read-out amplifier with baseline adaption 720 and signal amplification 730 stages correspond to adaptive sensor measurement circuit 1605. Signal amplification stages 736 and 740 correspond to gain stages 1610 and 1615, respectively.

Adaptive sensor measurement stage circuit 1605 is formed by an autozeroing element using a PMOS transistor M1 and an NPN bipolar transistor Q1 driving chemical sensor 1608. The steady-state operating point of the circuit is independent of the sensor resistance. If the sensor resistance changes due to analyte exposure, the equilibrium of the adaptive element is upset. This change is proportional to the percentage change of the resistance, and is amplified by AC-coupled floating gate amplifiers 1610 and 1615, permitting small changes in resistance to be detected.

The operating point of the adaptive sensor measurement stage will change to compensate for the new resistance on an adjustable time scale. Long-term changes in the baseline resistance of the sensor will be adapted out, but by controlling the time constants, this will insure the shorter term changes due to a desired analyte will be passed to the amplification stages. Large arrays of sensors on-chip may require transferring relatively large amounts of information on and off the chip for further processing. In FIG. 12, row and column multiplexers 1220 and 1230 are used to facilitate the communication of data from the sensors to other circuitry, on-chip or off-chip. As the arrays become larger and there are more sensors, there are much greater amounts of data to transfer, and specialized techniques may be used to improve the performance of the communication and transfer of the sensor data for further processing.

For example, in a typical analyte detection system, the sensors and adaptive electronics may be tightly coupled on a single chip. And the information from the sensors, after preprocessing by the adaptive electronics, is communicated off-chip to a standard microprocessor for neural network classification. In this case, there will be a relatively large number of signals to send off-chip. Alternatively, the sensors, adaptive electronics, and classification circuitry may all reside one chip. This gives a large number of signals to be routed on-chip.

Standard packaging technology, the limited number of pins on a chip, and the limited availability of routing resources severely limits the interchip and intrachip connectivity. Depending on the size of the array and the time available for processing, conventional multiplexing may be used for relatively small arrays, as shown in the architecture diagram of FIG. 12. Larger arrays may however require much higher compression of information. One technique, among others, that may be used by the communication protocol for interchip communication is the address event representation (AER) protocol. Address event representation was inspired by the success of time-division multiple-access (TDMA) protocols in communications and this TDMA-like protocol may be used to provide enhanced inter-chip and intrachip connectivity.

Time-division multiplexing trades time for space, using a single wire and some switches (i.e., transistors) to service several nodes. This approach pays off when wires are expensive and switches are cheap. By assigning each node a unique identifier, wires may be shared among the active nodes, allowing each node to transmit a uniquely labeled packet down the wire whenever it is active. The approach is especially effective when a small fraction of the population is active at any time. This sparse activity assumption holds for spike activity in neural systems, since neuronal spikes are extremely brief, neurons respond selectively, and neurons adapt. This approach is suitable for large arrays of chemical sensors, where clusters of sensors target specific analyte.

In address event representation, the circuit broadcasts the addresses specifying the location of neurons that fire as spikes occur. This encoding requires log2(N) wires instead of N wires, where N is the number of neurons or sensors. For example, in implementing address event representation, there may be one address-event sender chip and one address-event receiver chip, each having a 64-by-64 array of neurons. The communication channel provides virtual point-to-point connectivity between neurons at corresponding locations on these two chips. Arbitration and queuing mechanisms dealt with the collisions that occurred when multiple neurons attempted to transmit simultaneously. The address event representation technique yields very high peak throughput data transfer in the channel.

The address event protocol will enable the development of large arrays of analyte detection sensors that can communicate efficiently with other components of the system, such as the classifier. It is robust with respect to noise and attempts to maximize the available channel bandwidth while maintaining low hardware complexity.

The analyte detection system as shown in FIG. 9 of the present invention includes a classification stage or system to process the output of the sensor array and to identify the presence of the target analytes. To classify the analyte, one solution is to implement neural network classification algorithms in both software and hardware. It is desirable to integrate the classification neural network with the sensor array onto a single silicon chip, or onto a companion chip that communicates using the address event protocol discussed previously.

The classification stage of the analyte detection system may be linear or nonlinear. Linear approaches that may be used include computation of the nearest-distance Euclidian neighbor, discriminant technique, and other standard linear statistical techniques. Nonlinear approaches include neural network, genetic algorithms, and other nonlinear statistical techniques.

In a specific embodiment, the classification task involves feeding the preprocessed sensor outputs into a neural network classifier that then attempts to classify the analyte into one of a number of pretrained classes. In the simplest case the maximum response of the sensors, the peak of the resistance change, is fed to the network. The network then outputs a decision based on previous training corresponding to specific analytes. A more complex classifier might also use the time signature of the responses to make the classification decision.

Several different approaches to the classification problem may be utilized depending on the situation. First, if the classification is performed off-chip, such as in a microprocessor, standard back-propagation feed-forward networks, or recurrent networks if time signatures are to be utilized, may be used. Classification using dedicated analog integrated circuits, however, precludes the use of back-propagation and may require the development of other training and weight storage methods.

A feed-forward network has neurons arranged in layers. Each layer consists of neurons that receive their inputs from the previous layer and propagate their outputs to the layer above. Neurons in the same layer may or may not communicate with each other, although typically neurons do not communicate. The first layer is called the input layer: it receives the inputs from the outside world. The final layer is the output layer: their values are considered the result of the network. The layers between the input and output are called hidden layers.

Each unit performs a weighted summation of its inputs and passes the output through a nonlinear function to produce an output. It has been shown that selection of the proper weights can result in a network that can be used as a classifier. The selection of the weights is not based on any knowledge of the problem other than the desired outputs for a given input set. A training procedure adjusts randomly initialized weights until the error is minimized. There are many procedures for performing this training, but one of the most popular methods of training a neural network is back-propagation. The goal of this learning algorithm is to minimize the error at the outputs by adjusting the synaptic weights.

Training using back propagation has two phases. First, the inputs are presented to the network and the output is calculated. Next, the output is compared with the training data and the error computed according to the desired error function. The error is propagated backwards through the network to compute the weight derivatives for all the units. The weight derivatives can be accumulated and applied after presentation of the set of training data. Each pass through the training set is called an epoch.

Alternatively, the weights can be updated after each individual training vector, alleviating the need for high precision accumulation of the errors at the cost of a less accurate gradient descent. The training procedure is iterative. The training set is presented to the network until the error is minimized to an acceptable level. It is possible that the error can not be minimized. This can be due to being trapped in local minimums or can indicate that the network has too few units or layers. Possible solutions are to try again with a different set of initial weights, learning rates, or network size.

A major consideration in the choice of neural network architecture involves the number of sensors implemented, and the number of analytes that are required to be classified. If the number of sensors and classes is small, then it is feasible to consider directly feeding this number of inputs into a feed-forward classifier.

However, if the number of sensors and classes is large then it may not be possible to feed directly into a network because such a network would be overparameterized and may fail to generalize. Such a network would have a very high false alarm rate in classification as a result of overfitting to noise in the training data. For example, if a large network of 1000 sensors and 10 classes were implemented, a typical 3-layer feed forward network would contain, say, 20 hidden units. The number of weights in the network would be approximately 20,000. This would require at least 200,000 presentations of examples to train the weights. In such a case an intermediate stage of data reduction may need to be implemented in order to reduce the dimensionality of the input. This stage could utilize prior knowledge of the problem (e.g., by grouping chemically similar sensors), unsupervised clustering, principal component analysis, or auto-association clustering.

In each of the cases, a goal is to be able to reduce the size of the final classification network so that training the weights becomes practical in terms of the number of required training examples, the training time, or the degree of generalization and hence insensitivity to noise required to give robust classification.

Another technique for classification is using analog VLSI and a learning system. For example, an on-chip learning system would allow a chip to adapt to its environment. This is especially important in the application to chemical sensing, as it will allow the classifier to adapt to changes in the chemical sensors, and to differences in the manufacturing process. While the back-propagation algorithm discussed above is suitable for the task, it may not be practical for implementation in low-power analog integrated circuits. Back-propagation typically requires a high degree of accuracy, particularly in the error calculation stage. Unfortunately, high precision computation are generally difficult in analog circuitry due to the inherent mismatch of the devices and noise.

A different technique may be used for analog hardware. In practice, it is difficult to implement analog VLSI applications of on-chip classifiers because: (1) there is a lack of suitable memory devices capable of changing and storing a weight in a nonvolatile fashion, and (2) classification algorithms require a high degree of precision in order to perform in-situ or on-chip learning. With any neural classification system it is necessary to store analog weights. Digital implementations in microprocessors or digital signal processing (DSP) chips store these weights digitally and perform the learning calculations via computer arithmetic circuits. Much more efficient learning hardware can be obtained by storing the weight in analog circuitry (such as the technique with the floating gate device discussed above) and using analog addition and subtraction of weight increments. An analyte detection system with a classification system implemented in analog VLSI is further enhanced by the use of nonvolatile analog memory elements.

An analog memory may be implemented in a similar fashion as discussed for the floating gate technologies employed in the autozeroing amplifiers, shown in FIGS. 14–15. The memory cell uses the tunneling and injection processes to store charge on an isolated gate that can retain the charge for hundreds of years. The memory requires no quiescent power to store a value, and therefore will retain the programmed value after removal of the power supply to the memory cell.

The neural classification system may use a learning algorithm called "perturbative learning." Perturbative learning is more suitable for analog hardware, and can utilize the analog memory. Instead of computing the error, as in backpropagation, this perturbative learning circuitry will actually measure the error. Each weight has a small perturbation, applied, and the resulting change in the output error is measured. All the weights in the network are perturbed by a perturbation of equal magnitude but of random sign. By keeping the weight perturbation magnitudes small, and the sign of the perturbations uncorrelated, this technique can approximate the back-propagation of errors algorithm without the precision-requiring step of computing the gradient and propagating it backwards through the network.

An advantage of this method, particularly for implementation in analog hardware, is its simplicity. No gradient calculations are performed, and there is no requirement to propagate the error back through the network. It is much easier to measure the error than to calculate it. Each weight is perturbed by a random value, and the output error is measured. If the error decreases, the perturbation is saved. If the error increases, then the weights are not changed. This procedure is repeated for all training patterns until the network performance is acceptable. One drawback of this method is that by perturbing all the weights in the network simultaneously, the error due to each individual weight is not measured, but rather the error due to all of the weights in the networks is measured. However, by having uncorrelated perturbations, statistically, this algorithm tends to gradient descent as training progress.

A sensor of the present invention, such as that shown in FIG. 7, may also be used with electronics that measure capacitance of the sensor to detect the presence of analytes, or to differentiate between different analytes. As described above, the sensor expands in the presence of an analyte. As the size of the sensor changes, the capacitance of the sensor changes also. Thus, by measuring the capacitance, the presence of the analyte may be determined. The techniques described above with regard to determining a "fingerprint" with an array of sensors may be used with the capacitive measurement as the operative variable.

Figure 17:
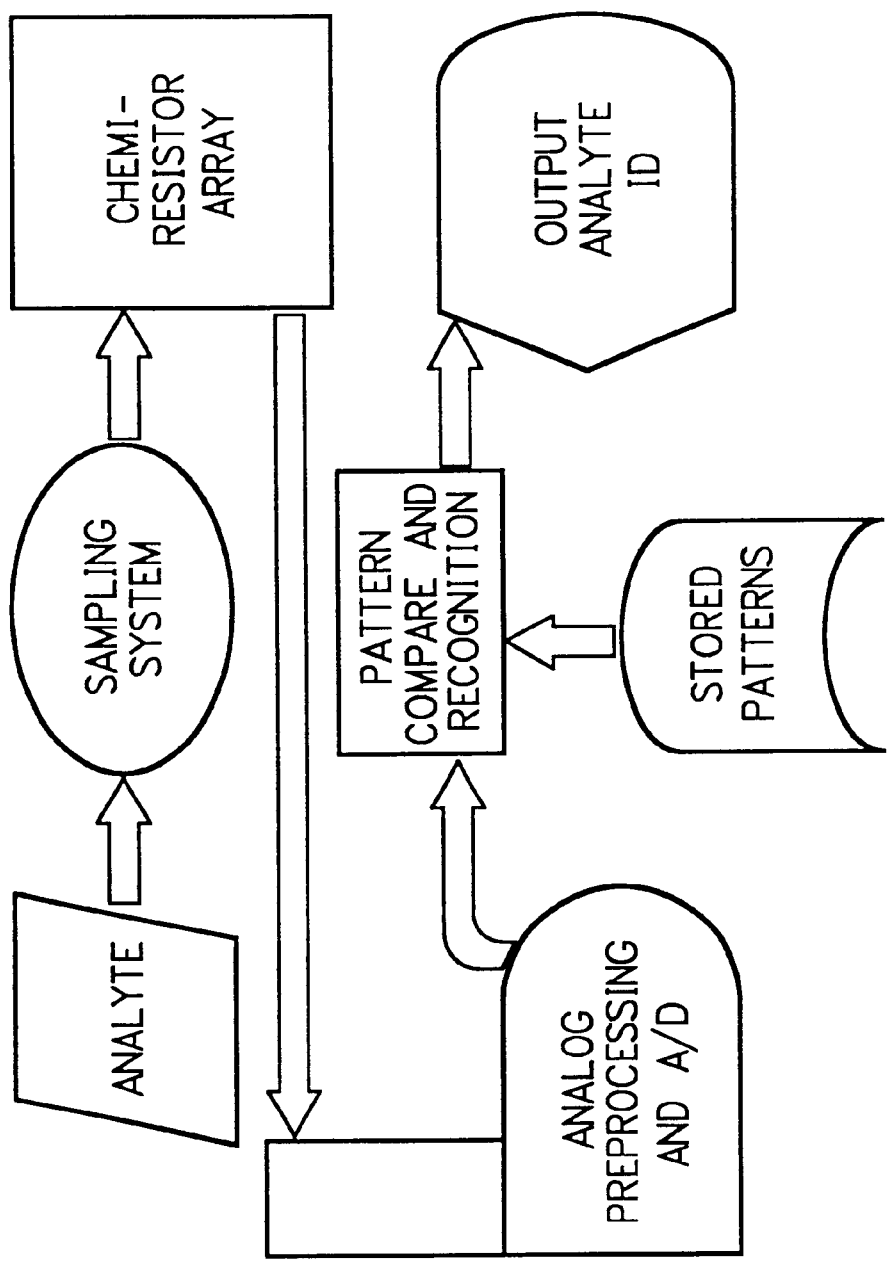
FIG. 17 shows a block diagram of an analyte detection system.

FIG. 17 shows a block diagram of an analyte detection system. The block diagram for a discrete system that has been developed are shown in the analyte detection system block diagram and system design. Any full analyte sampling system should include a means for sampling the analyte of interest. This could be as simple as a stick to attach the sensors and a means for holding it in the vicinity of a vapor of interest, or as complex as a network of pumps and valves sequencing through a complex sampling routine. Once the analyte has been presented to the array of chemically sensitive transducers, the signals are processed and presented to an A/D converter. The pattern of response across the array is then compared to a stored pattern of response and an identification can be made through any number of possible input output channels as simple as wires to a control system or as complex as a visual display system.

Figure 18:
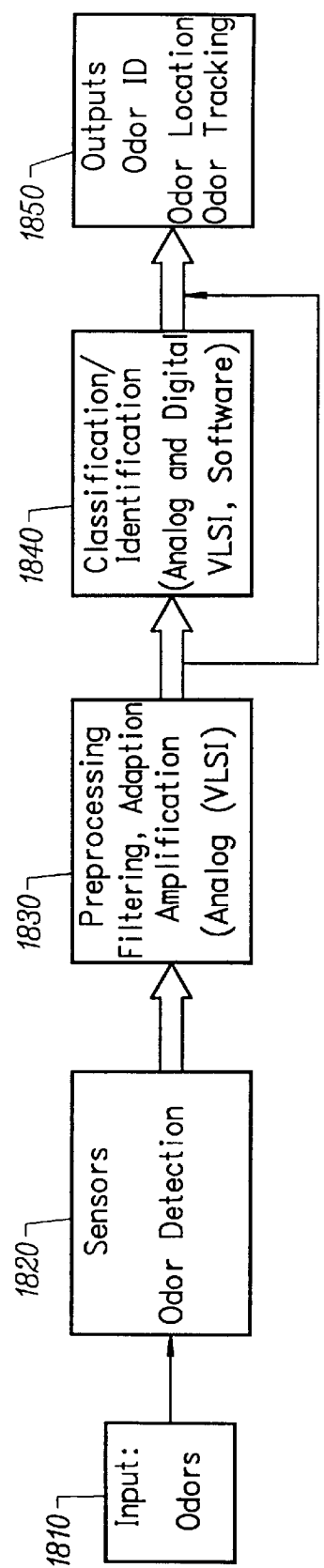
FIG. 18 shows a block diagram of an analyte detection system of the present invention.

FIG. 18 shows a block diagram showing a flow diagram of a technique for analyte detection and identification according the present invention. An analyte or odorant 1810 is input to the sensors 1820. An analyte detection sensor chip such as described above may be used in the detection of the analyte.

The signals from the sensors are preprocessed 1830 using preprocessing circuitry. The preprocessing step or stage performs a number of tasks which may include: translation of the sensor response into an electrical signal, adaptive gain and baseline adjustment, intersensor arraying for filtering, failure robustness, and global gain adjustment. In one embodiment, the preprocessing circuitry may be off-chip, located separately from the sensor array. In another embodiment, the electronic preprocessing may be closely coupled with the sensor and with the sensor array as a whole. For example, the preprocessing circuitry may be on-chip with the sensor array. The circuitry may be interspersed, interleaved, or otherwise integrated on-chip with the sensors. Furthermore, the preprocessing circuitry may be formed beneath the sensor sites as described above. In one embodiment, the preprocessing circuitry is implemented using analog VLSI circuitry.

For resistance sensors, the preprocessing circuitry may provide the ability to adapt to changes in temperature, humidity, and other conditions that will affect the nominal resistance of the sensor. Adapting the sensors and circuitry to the environment is important or else long time-scale changes would erroneously be reported as the presence of analytes. In addition, the preprocessing circuitry may stabilize the operation of sensors that are fabricated with characteristics near a percolation threshold. This would enable orders of magnitude increase in sensitivity, if such is needed.

Adaptation and learning are important aspects of a system of the present invention. The early stages for processing the analyte information are generally data-driven and require short-term adaptation. At this stage, adaptation compensates for sensor and local device variations, and permits adaption to highly variable signal levels to extract the limited signal dynamic range that contains useful information. Later stages in the processing, such as scene analysis and recognition stages, may use long-term adaptation and learning. These later stages may make use of prior knowledge.

For adaptation circuitry to be effective, it is desirable to have relatively rapid sensor response times. Then, long-term drift in the response of the sensors may be rejected since this is unwanted. And, large gradients in the signal can then be used to focus on the desired change detection signals arising from the analytes or vapors in the environment.

Since swelling of the sensor material begins after exposure to the analyte or vapor, the resistance or capacitance (or other property) signals can be read in real time or near real time. Currently, with films on the order of one micron in thickness, the swelling (and therefore change in resistance and capacitance) response times to equilibrium film swelling range from less than about 0.1 seconds to greater than about 100 seconds, depending on the analyte and sensor material through which the analyte diffuses.

Characteristic patterns may be produced even at times shorter than equilibrium, since the time-dependent swelling properties also provide diagnostic pattern information on the analyte of interest. The pattern may be read out after a fixed exposure time, and it is not necessary that equilibrium be reached for all sensors in order to obtain the characteristic fingerprint of the analyte.

More rapid responses to equilibrium may be obtained by reducing a film thickness of the sensor material applied to the chip. Since the diffusion time is proportional to the square of the film thickness (if Fickian diffusion is obeyed), decreasing the film thickness to the range of 0.1 micron should provide real-time responses for most analytes when using a sensor array. It should be noted this response time is much more rapid than can be achieved using other detection methods such as: gas chromatographic methods, biosensors that require transfer of particles or vapors into the liquid phase, or most other approaches to chemical detection of for example, land mine signatures.

The preprocessing circuitry generates output signals to be used by a classification and identification stage 1840. This stage may be implemented using on-chip circuitry, or alternatively, using off-chip circuitry or systems. Moreover, portions of this stage may be on-chip, while other portions are off-chip. The identification and classification of the analyte may be determined using analog or digital VLSI circuitry, or combinations of analog and digital VLSI circuitry. Software and a computer may also be used to perform identification and classification.

Outputs 1850 from the preprocessing stage or classification/identification stage, or both, may further be used to control or implement a multitude of other functions. For example, the analyte detection technique of the present invention may be used by a mobile or portable electronic device such as a robot to track a plume trail of analyte to its source. This robot may be able to, for example, identify the location of a land mine. There are many other functions and operations that may be controlled based on the outputs from a an analyte detection device.

The components and stages used to implement the analyte detection system shown in FIG. 18 may reside on separate integrated circuits or electronic subsystems. These subsystems may be separate integrated circuits that communicate with another through, for example, interconnections on a printed circuit or board, or even through a network (e.g., local area network, wide area network, satellite network, the internet).

The entire system may also be implemented within a single integrated circuit, or several integrated circuits. For example, the analyte detection system may be embodied within what is commonly referred to as a "chipset." This chipset may include two, three, four, or more integrated circuits. Original equipment manufacturers (OEMs) may use an analyte detection chipset of the present invention to build a system incorporating the analyte detection technique of the present invention.

Moreover, a system of the present invention may be implemented entirely on a single integrated circuit. As integrated circuit technology advances, integrated circuits provide greater and greater functionality per chip. In such a single integrated circuit analyte detection system, the various components of the system will communicate through the interconnect of the chip. The interconnect on the integrated circuit may be metal such as aluminum or copper conductors.

The foregoing description of preferred embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize and practice the invention in various embodiments and with various modifications as are suited to the particular use contemplated. It is intended that the scope of the invention be defined by the following claims.

What is claimed is:

1. A circuit for an analyte detection system comprising:
a sensor site wherein sensor material is constrained at the sensor site and has regions of a nonconductive organic material and a conductive material, and in the presence of an analyte, the sensor material has a measurable change in an electrical property; and
a floating gate device coupled to the sensor site, wherein the floating gate device stores an analog value, representative of the measurable chance in the electrical property from the sensor site, based on an amount of charge on a floating gate of the floating gate device; and
the analog value is used by the analog detection system to determine the presence of the analyte.

2. The circuit of claim 1 further comprising:
a first transistor coupled between a first supply voltage and a first node, wherein a gate of the first transistor is coupled to the floating gate device; and
a second transistor coupled between the first node and a second supply voltage, wherein a gate of the second transistor is coupled to a bias voltage.

3. The circuit of claim 2 wherein the first transistor is a PMOS device and the second transistor is an NMOS device.

4. The circuit of claim 2 further comprising:
a capacitor coupled between the first node and the floating gate device.

5. The circuit of claim 1 wherein the floating gate device stores an analog value with about 14 bits or greater of accuracy.

6. The circuit of claim 1 wherein the floating gate device stores an analog value having 14 bits or less of accuracy.

7. The circuit of claim 1 wherein the floating gate device provides nonvolatile storage.

8. The circuit of claim 1 wherein the floating gate device operates in the subthreshold regime.

* * * * *